US012648903B2

(12) United States Patent
Richter et al.

(10) Patent No.: US 12,648,903 B2
(45) Date of Patent: *Jun. 9, 2026

(54) SKIN CARE COMPOSITION

(71) Applicants: BEIERSDORF AG, Hamburg (DE);
S-BIOMEDIC, Beerse (BE)

(72) Inventors: Daniel Richter, Niederfrohna (DE);
Jennifer Huepeden, Hamburg (DE);
Joern Hendrik Reuter,
Henstedt-Ulzburg (DE); Heike Foelster,
Hamburg (DE); Bernhard Felten,
Pinneberg (DE); Jane Djamil, Hamburg
(DE); Peter Steidle, Hamburg (DE);
Petra Schoendienst, Tornesch (DE);
Tina Hamann, Brodersby-Goltoft (DE);
Stefan Gallinat, Wedel (DE); **Willy
Verheyen, Vosselaar (DE); João Pedro
Quintão Reis Pereira De Lima**,
Antwerp (BE); **Bernhard Felix
Paetzold**, Berchem (BE)

(73) Assignees: S-BIOMEDIC, Beerse (BE);
BEIERSDORF AG, Hamburg (DE)

( * ) Notice: Subject to any disclaimer, the term of this
patent is extended or adjusted under 35
U.S.C. 154(b) by 816 days.

This patent is subject to a terminal dis-
claimer.

(21) Appl. No.: 17/754,432

(22) PCT Filed: Dec. 18, 2019

(86) PCT No.: PCT/EP2019/085882
§ 371 (c)(1),
(2) Date: Apr. 1, 2022

(87) PCT Pub. No.: WO2021/063531
PCT Pub. Date: Apr. 8, 2021

(65) Prior Publication Data
US 2022/0354776 A1 Nov. 10, 2022

(30) Foreign Application Priority Data
Oct. 3, 2019 (EP) .................................... 19201258

(51) Int. Cl.
| | |
|---|---|
| *A61K 8/99* | (2017.01) |
| *A61K 8/04* | (2006.01) |
| *A61K 8/34* | (2006.01) |
| *A61K 8/67* | (2006.01) |
| *A61K 8/73* | (2006.01) |
| *A61K 8/92* | (2006.01) |
| *A61Q 17/00* | (2006.01) |
| *A61Q 19/00* | (2006.01) |

(52) U.S. Cl.
CPC .................. *A61K 8/99* (2013.01); *A61K 8/04*
(2013.01); *A61K 8/34* (2013.01); *A61K 8/678*
(2013.01); *A61K 8/732* (2013.01); *A61K 8/92*
(2013.01); *A61Q 17/005* (2013.01); *A61Q
19/00* (2013.01)

(58) Field of Classification Search
CPC ... A61K 8/99; A61K 8/04; A61K 8/34; A61K
8/678; A61K 8/732; A61K 8/92; A61K
47/06; A61K 47/22; A61K 47/26; A61K
8/86; A61K 9/0014; A61K 47/02; A61K
47/10; A61K 47/14; A61K 47/32; A61K
47/36; A61K 47/38; A61K 47/44; A61K
2800/49; A61K 47/34; A61K 35/74;
A61Q 17/005; A61Q 19/00; A61Q
19/008; A61Q 5/006; A61P 17/06; A61P
17/08; A61P 17/10
See application file for complete search history.

(56) References Cited

U.S. PATENT DOCUMENTS

| | | | |
|---|---|---|---|
| 6,743,609 B1 | 6/2004 | Rosson et al. | |
| 2005/0186583 A1 | 8/2005 | Rosson et al. | |
| 2006/0073106 A1* | 4/2006 | Berg-Schultz | A61Q 17/04 424/59 |
| 2009/0099075 A1* | 4/2009 | Barg | A61Q 19/08 435/252.8 |

(Continued)

FOREIGN PATENT DOCUMENTS

| | | | | |
|---|---|---|---|---|
| CN | 104784058 A | * | 7/2015 | |
| CN | 105434307 A | | 3/2016 | |
| CN | 107303259 A | | 10/2017 | |
| DE | 102015207624 A1 | * | 10/2016 | A61K 8/342 |

(Continued)

OTHER PUBLICATIONS

Dréno et al. (JEADV 2018, 32 (Suppl. 2), 5-14; Accepted: Mar. 6,
2018) (Year: 2018).*

(Continued)

*Primary Examiner* — Robert A Wax
(74) *Attorney, Agent, or Firm* — Abel Schillinger, LLP

(57) ABSTRACT

The present invention generally relates to the field of skin
care. More particularly, the invention relates to a cosmetic or
therapeutic skin care composition comprising live bacteria
of at least one *Cutibacterium acnes* (*C. acnes*) strain in
combination with a solubilizer that specifically supports
their viability during storage and/or their ability to replicate
after application to the skin. Preferably, the cosmetic or
therapeutic skin care composition comprises bacteria of at
least one *C. acnes* strain selected from the group consisting
of D1, A5, C1, C3, H1, H2, H3, K1, K2, K4, K6, K8, K9,
L1, and F4. The invention also provides a method for
treating or preventing acne by applying the skin care com-
position of the invention to a skin area in need of treatment.
The invention also relates to the use of a skin care compo-
sition of the invention for treating or preventing acne.

20 Claims, 5 Drawing Sheets
Specification includes a Sequence Listing.

(56) References Cited

U.S. PATENT DOCUMENTS

| | | | | |
|---|---|---|---|---|
| 2011/0081401 A1* | 4/2011 | Panzieri et al. | | |
| 2016/0326091 A1 | 11/2016 | Rudolph et al. | | |
| 2016/0374352 A1* | 12/2016 | Modak | ................. | A61K 31/155 424/54 |
| 2017/0143774 A1 | 5/2017 | Mulder et al. | | |
| 2018/0021229 A1 | 1/2018 | Gasparri et al. | | |
| 2018/0078588 A1 | 3/2018 | Taylor et al. | | |
| 2018/0142202 A1 | 5/2018 | Patzold et al. | | |
| 2019/0314428 A1 | 10/2019 | Patzold et al. | | |
| 2020/0121444 A1 | 4/2020 | Li et al. | | |
| 2021/0251885 A1 | 8/2021 | Richter et al. | | |
| 2021/0284431 A1 | 9/2021 | Felten | | |
| 2022/0331374 A1 | 10/2022 | Richter et al. | | |
| 2022/0339094 A1 | 10/2022 | Richter et al. | | |
| 2022/0395451 A1 | 12/2022 | Richter et al. | | |
| 2023/0038623 A1 | 2/2023 | Richter et al. | | |

FOREIGN PATENT DOCUMENTS

| | | | | | |
|---|---|---|---|---|---|
| EP | 1389459 A1 | * | 2/2004 | ............ | A61K 8/732 |
| EP | 3061501 A1 | | 8/2016 | | |
| FR | 2957788 A | | 9/2011 | | |
| GB | 2386604 A | * | 9/2003 | ............... | A61K 8/02 |
| WO | WO-2013130829 A1 | * | 9/2003 | ............... | A61K 8/99 |
| WO | 2016172196 A1 | | 10/2016 | | |
| WO | WO-2018073651 A1 | * | 4/2018 | ........... | A61K 35/741 |
| WO | 2018077598 A1 | | 5/2018 | | |
| WO | 2018089337 A1 | | 5/2018 | | |
| WO | 2019238968 A1 | | 12/2019 | | |

OTHER PUBLICATIONS

English translation of Su, CN 104784058 A (Year: 2015).*

Database GNPD [Online] MINTEL; Jul. 25, 2012 (Jul. 25, 2012). anonymous: SOS Spot Corrector retrieved from www.gnpd.com, Database accession No. 1843445.

Bek-Thomsen, M., Lomholt, H.B., and Kilian, M. (2008). Acne is not associated with yet-uncultured bacteria. J. Clin. Microbial. 46, pp. 3355-3360.

Belkaid, Y., and Segre, J.A. (2014). Dialogue between skin microbiota and immunity. Science 346, pp. 954-959.

Downing, D.T., Stewart, M.E., Wertz, P.W., and Strauss, J.S. (1986). Essential fatty acids and acne. J. Am. Acad. Dermatol. 14, pp. 221-225.

Fitz-Gibbon, S., Tomida, S., Chiu, B.-H., Nguyen, L., Du, C., Liu, M., Elashoff, D., Erfe, M.C., Loncaric, A., Kim, J., et al. (2013). Propionibacterium acnes strain populations in the human skin microbiome associated with acne. J. Invest. Dermatol. 133, pp. 2152-2160.

Grice, E.A., and Segre, J.A. (2011). The skin microbiome. Nat. Rev. Microbial. 9, pp. 244-253.

Holmes, AD. (2013). Potential role of microorganisms in the pathogenesis of rosacea. J. Am. Acad. Dermatol. 69, pp. 1025-1032.

Kong, H.H., Oh, J., Deming, C., Conlan, S., Grice, E.A., Beatson, M.A., Nomicos, E., Polley, E.C., Komarow, H.D., Murray, P.R., et al. (2012). Temporal shifts in the skin microbiome associated with disease flares and treatment in children with atopic dermatitis. Genome Res. 22, pp. 850-859.

Letawe, C., Boone, M., and Pierard, G.E. (1998). Digital image analysis of the effect of topically applied linoleic acid on acne microcomedones. Clin. Exp. Dermatol. 23, pp. 56-58.

Lomholt, H.B., and Killan, M. (2010). Population Genetic Analysis of Propionibacterium acnes Identifies a Subpopulation and Epidemic Clones Associated with Acne. PLoS ONE 5.

McDowell, A., Barnard, E., Nagy, 1., Gao, A., Tomida, S., Li, H., Eady, A., Cove, J., Nord, C.E., and Patrick, S. (2012). An Expanded Multilocus Sequence Typing Scheme for Propioni-bacterium acnes: Investigation of "Pathogenic", "Commensal" and Antibiotic Resistant Strains. PLoS ONE 7, e41480.

Oh, J., Byrd, A.L., Deming, C., Conlan, S., NISC Comparative Sequencing Program, Kong, H.H., and Segre, J.A. (2014). Biogeography and individuality shape function in the human skin metagenome. Nature 514, pp. 59-64.

Scholz, C.F.P., Jensen, A., Lomholt, H.B., Bruggemann, H., and Killan, M. (2014). A Novel High-Resolution Single Locus Sequence Typing Scheme for Mixed Populations of Propioni-bacterium acnes In Vivo. PLoS ONE 9, e104199.

Himanshu K. Solanki et al.: "Development of Microencapsulation Delivery System for Long-Term Preservation of Probiotics as Biotherapeutics Agent" Biomed Research International. vol. 2013. Jan. 1, 2013 (Jan. 1, 2013). pp. 1-21.

Database GNPD [Online] MINTEL; Mar. 9, 2018 (Mar. 9, 2018). anonymous: "Peach Yogurt" retrieved from www.gnpd.com Database accession No. 5509333 abstract.

U.S. Appl. No. 17/754,433, National Stage of PCT/EP2019/085884, filed Dec. 18, 2019.

U.S. Appl. No. 17/754,426, National Stage of PCT/EP2019/085873, filed Dec. 18, 2019.

* cited by examiner

| INCI | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
|  |  |  |  |  |  |  |  | [%] |  |  |  |  |  |  |  |
| alcohol denat. |  |  | 8.040 |  | 8.152 | 8.152 | 8.152 | 8.152 | 10.211 |  | 10.536 | 9.740 | 9.740 | 9.740 | 9.740 |
| butylene glycol |  |  |  |  |  |  |  | 3.760 |  |  |  |  |  |  |  |
| C. acnes lyophilisate | 2.800 | 2.800 | 2.800 | 2.800 | 2.800 | 2.800 | 2.800 | 2.800 | 2.800 | 2.800 | 2.800 | 0.940 | 0.940 | 0.940 | 0.940 |
| caprylyl glycol |  |  |  |  |  |  | 0.075 | 0.075 |  |  | 0.094 |  |  |  |  |
| carbomer |  |  |  |  |  |  | 0.564 |  |  |  |  |  |  |  |  |
| chondrus crispus extract | 1.000 | 1.000 | 1.000 | 0.075 |  |  |  |  | 1.000 | 1.000 |  |  |  |  |  |
| citric acid | 0.015 | 0.084 | 0.015 | 0.015 | 0.015 | 0.008 | 0.008 | 0.008 | 0.018 | 0.018 | 0.018 | 0.017 | 0.017 | 0.017 | 0.017 |
| dicaprylyl carbonate |  |  |  |  |  |  |  |  |  |  |  |  | 7.500 |  |  |
| dicaprylyl ether |  |  |  |  |  |  |  |  |  |  |  |  |  |  | 7.500 |
| distarch phosphate | 2.000 | 2.000 | 2.000 | 2.000 | 2.000 | 2.000 | 2.000 | 2.000 | 2.000 | 2.000 |  | 2.000 | 2.000 | 2.000 | 2.000 |
| ethylhexyl cocoate |  |  |  |  |  |  |  |  |  |  |  | 10.000 | 7.500 |  |  |
| glycerin |  | 5.565 | 5.565 | 5.640 | 5.640 | 5.640 | 3.760 | 3.760 | 7.085 | 7.085 | 7.290 | 6.225 | 6.225 | 6.225 | 6.225 |
| hydroxyethylcellulose |  |  |  |  | 0.451 |  |  |  |  |  | 0.583 | 0.498 | 0.498 | 0.498 | 0.498 |
| hydroxypropyl starch phosphate |  |  |  | 3.384 |  |  |  |  |  |  |  |  |  |  |  |
| isododecyl neopentanoate |  |  |  |  |  |  |  |  |  |  |  |  |  | 10.000 |  |
| isopropyl palmitate | 20.000 | 20.000 | 20.000 | 20.000 | 20.000 | 20.000 | 20.000 | 20.000 |  |  |  | 5.000 |  | 5.000 | 7.500 |
| methylpropanediol |  |  |  |  |  |  |  |  |  | 3.768 |  |  |  |  |  |
| phenoxyethanol |  |  |  |  |  |  |  |  |  | 0.188 |  |  |  |  |  |
| sodium chloride | 0.900 | 0.668 | 0.868 | 0.677 | 0.677 | 0.677 | 0.677 | 0.677 | 0.848 | 0.848 | 0.875 | 0.747 | 0.747 | 0.747 | 0.747 |
| sodium citrate | 0.174 | 0.129 | 0.129 | 0.131 | 0.131 | 0.131 | 0.131 | 0.131 | 0.164 | 0.164 | 0.169 | 0.144 | 0.144 | 0.144 | 0.144 |
| sodium hyaluronate |  |  |  |  |  |  | 0.378 | 0.978 |  |  |  |  |  |  |  |
| aqua | ad 100 |  |  |  |  |  |  |  |  |  |  |  |  |  |  |  |

FIG. 1

| INCI | C | 1 | 2 | 3 | 4 | 5 | 6 | 7 | 8 | 9 | 10 | 11 |
|---|---|---|---|---|---|---|---|---|---|---|---|---|
| lyophilisate | 4.710 | 4.710 | 4.710 | 4.710 | 4.710 | 4.710 | 4.710 | 4.710 | 4.710 | 4.710 | 4.710 | 4.710 |
| isopropyl palmitate | 0.050 | 0.050 | 0.050 | 0.050 | 0.050 | 0.050 | 0.050 | 0.050 | 0.050 | 0.050 | 0.050 | 0.050 |
| ethylhexyl cocoate | 0.050 | 25.000 | 0.050 | 0.050 | 0.050 | 0.050 | 0.050 | 0.050 | 0.050 | 0.050 | 0.050 | 0.050 |
| distarch phosphate | 0.050 | 0.050 | 5.000 | 0.050 | 0.050 | 0.050 | 0.050 | 0.050 | 0.050 | 0.050 | 0.050 | 0.050 |
| glycerin | 0.050 | 0.050 | 0.050 | 0.050 | 0.050 | 0.050 | 0.050 | 0.050 | 0.050 | 0.050 | 0.050 | 0.050 |
| citric acid | 0.010 | 0.010 | 0.010 | 0.010 | 0.010 | 0.010 | 0.010 | 0.010 | 0.010 | 0.010 | 0.010 | 0.010 |
| sodium citrate | 0.010 | 0.010 | 0.010 | 0.010 | 0.010 | 0.010 | 0.010 | 0.010 | 0.010 | 0.010 | 0.010 | 0.010 |
| sodium chloride | 0.050 | 0.050 | 0.050 | 0.050 | 0.050 | 0.050 | 0.050 | 0.050 | 0.050 | 0.050 | 0.050 | 0.050 |
| hydroxyethylcellulose | 0.050 | 0.050 | 0.050 | 0.050 | 0.050 | 0.050 | 0.050 | 0.050 | 0.050 | 0.050 | 0.050 | 0.050 |
| ethanol + aqua | 0.500 | 0.500 | 0.500 | 20.000 | 0.500 | 0.500 | 0.500 | 0.500 | 0.500 | 0.500 | 0.500 | 0.500 |
| PEG-40 hydrogenated castor oil | 0.010 | 0.010 | 0.010 | 0.010 | 2.500 | 0.010 | 0.010 | 0.010 | 0.010 | 0.010 | 0.010 | 0.010 |
| aqua | 94.460 | 69.510 | 89.510 | 74.960 | 91.970 | 94.460 | 94.460 | 94.460 | 94.460 | 94.460 | 94.460 | 94.460 |
| sodium hydroxide + aqua | 0.001 | 0.001 | 0.001 | 0.001 | 0.001 | 0.001 | 0.001 | 0.001 | 0.001 | 0.001 | 0.001 | 0.001 |
| dicaprylyl carbonate | | | | | 25.000 | | | | | | | |
| Chondrus crispus extract | | | | | | 7.500 | | | | | | |
| Hydroxypropyl starch phosphate | | | | | | | 10.000 | | | | | |
| tocopherol | | | | | | | | 2.000 | | | | |
| tocopheryl acetate | | | | | | | | | 2.000 | | | |
| tapioca starch | | | | | | | | | | | 5.000 | |
| phenoxyethanol | | | | | | | | | | | | 0.230 |
| caprylyl glycol | | | | | | | | | | | | 0.180 |
| methylpropanediol | | | | | | | | | | | | 4.000 |

FIG. 4

| Formulation | CFU/mL at t0 (0h) | CFU/mL at t1 (1h) |
|---|---|---|
| Control | 9.2E+08 | 8.4E+08 |
| 1 | 1.3E+09 | 2.8E+09 |
| 2 | 2.7E+09 | 1.0E+09 |
| 3 | 9.6E+08 | 1.5E+09 |
| 4 | 1.8E+09 | 1.6E+09 |
| 5 | 2.4E+09 | 1.0E+09 |
| 6 | 3.9E+09 | 3.2E+09 |
| 7 | 2.8E+09 | 1.8E+09 |
| 8 | 7.2E+08 | 7.2E+08 |
| 9 | 9.5E+08 | 9.3E+08 |
| 10 | 1.0E+09 | 7.9E+08 |
| 11 | 7.9E+08 | 7.5E+08 |

FIG. 5

| Formulation | INCI | Substance class | CFU/mL at t0 (0h) | CFU/mL at t1 (1h) | CFU/mL at t6 (6h) |
|---|---|---|---|---|---|
| Control | | | 1,5E+09 | | 1,1E+09 |
| V-1 | Paraffinum liquidum | emollient | 1.3E+09 | | 4.0E+08 |
| V-2 | Octyldodecanol | emollient | 2.5E+09 | | 1.0E+08 |
| V-3 | Talc | filler | 2.4E+09 | | 8.5E+08 |
| V-4 | Polymethyl silsesquioxane | filler | 1.6E+09 | | 7.5E+08 |
| V-5 | Carbomer | thickener | 1.6E+09 | 1.0E+06 | |
| V-6 | Alkyl/Acrylate Crosspolymer | thickener | 6.0E+08 | 3.8E+08 | |
| V-7 | Ascorbic Acid | antioxidant | 9.1E+08 | <1.0E+05 | |
| V-8 | Benzethonium Chloride | preservative | 1.4E+08 | 9.7E+07 | |
| V-9 | Caprylyl/Capryl Glucoside | solubilizer | 1.9E+09 | 3.1E+07 | |
| V-10 | Glyceryl Caprylate | solubilizer | 1.2E+09 | <1.0E+05 | |

FIG. 6

| INCI | C | V-1 | V-2 | V-3 | V-4 | V-5 | V-6 | V-7 | V-8 | V-9 | V-10 |
|---|---|---|---|---|---|---|---|---|---|---|---|
| lyophilisate | 4.710 | 4.710 | 4.710 | 4.710 | 4.710 | 4.710 | 4.710 | 4.710 | 4.710 | 4.710 | 4.710 |
| isopropyl palmitate | 6.250 | | | 6.250 | 6.250 | 6.250 | 6.250 | 6.250 | 6.250 | 6.250 | 6.250 |
| ethylhexyl cocoate | 12.500 | | | 12.500 | 12.500 | 12.500 | 12.500 | 12.500 | 12.500 | 12.500 | 12.500 |
| distarch phosphate | 2.500 | 2.500 | 2.500 | | | 2.500 | 2.500 | 2.500 | 2.500 | 2.500 | 2.500 |
| hydroxyethylcellulose | 0.44424 | 0.44424 | 0.44424 | 0.44424 | 0.44424 | | | 0.44424 | 0.44424 | 0.44424 | 0.44424 |
| ethanol + aqua | 9.6252 | 9.6252 | 9.6252 | 9.6252 | 9.6252 | 9.6252 | 9.6252 | 9.6252 | | 9.6252 | 9.6252 |
| PEG-40 hydrogenated castor oil | 0.3702 | 0.3702 | 0.3702 | 0.3702 | 0.3702 | 0.3702 | 0.3702 | 0.3702 | 0.3702 | | |
| aqua | 57.22478 | 57.22478 | 57.22478 | 57.22 | 57.22 | 57.23 | 57.23 | 54.22 | 66.76 | 56.59 | 57.29497 |
| glycerin | 5.553 | 5.553 | 5.553 | 5.553 | 5.553 | 5.553 | 5.553 | 5.553 | 5.553 | 5.553 | 5.553 |
| citric acid | 0.01481 | 0.01481 | 0.01481 | 0.01481 | 0.01481 | 0.01481 | 0.01481 | 0.01481 | 0.01481 | 0.01481 | 0.01481 |
| sodium citrate | 0.12883 | 0.12883 | 0.12883 | 0.12883 | 0.12883 | 0.12883 | 0.12883 | 0.12883 | 0.12883 | 0.12883 | 0.12883 |
| sodium chloride | 0.66636 | 0.66636 | 0.66636 | 0.66636 | 0.66636 | 0.66636 | 0.66636 | 0.66636 | 0.66636 | 0.66636 | 0.66636 |
| sodium hydroxide + Aqua | 0.01259 | 0.01259 | 0.01259 | 0.01259 | 0.01259 | 0.01259 | 0.01259 | 0.01259 | 0.01259 | 0.01259 | 0.01259 |
| paraffinum liquidum | | 18.750 | | | | | | | | | |
| octyldodecanol | | | 18.750 | | | | | | | | |
| talc | | | | 2.500 | | | | | | | |
| polymethylsilsesquioxane | | | | | 2.500 | | | | | | |
| carbomer | | | | | | 0.440 | | | | | |
| alkyl acrylate crosspolymer | | | | | | | 0.440 | | | | |
| ascorbic acid | | | | | | | | 3.000 | | | |
| trisodium EDTA + aqua | | | | | | | | | | | |
| benzethonium chloride | | | | | | | | | 0.090 | | |
| decylene glycol | | | | | | | | | | | |
| caprylyl/capryl glucoside | | | | | | | | | | 1.000 | |
| glyceryl caprylate | | | | | | | | | | | 0.300 |

FIG. 7

SEQUENCE LISTING

<160> NUMBER OF SEQ ID NOS: 82

<210> SEQ ID NO 1
<211> LENGTH: 484
<212> TYPE: DNA
<213> ORGANISM: Propionibacterium acnes

<400> SEQUENCE: 1

```
gttgcacacc aggggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgcccttta ttagggcaag cggtgccagt agcagaatat     360
gtcacctcaa caactcgatc cacccctgcc cattacatgg gtaacatatc catggaggtt     420
cgatgtatac tcgaggatac agtcgtccat cacgcccgcc tacatacccca ttacatcagc     480 atag                                                                   484
```

<210> SEQ ID NO 2
<211> LENGTH: 484
<212> TYPE: DNA
<213> ORGANISM: Propionibacterium acnes

<400> SEQUENCE: 2

```
gttgcacacc aggggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgattctg gattcctatt gtcgcccttta ttagggcaag cggtgccagt agcagaatat     360
gtcacctcaa caactcgatc cacccctgcc cattacatgg gtaacatatc catggaggtt     420
cgatgtatac tcgaggatac agtcgtccat cacgcccgcc tacatacccca ttacatcagc     480 atag                                                                   484
```

```
<210> SEQ ID NO 3
<211> LENGTH: 484
<212> TYPE: DNA
<213> ORGANISM: Propionibacterium acnes

<400> SEQUENCE: 3
gttgcacacc agggggtcaa cttggcgtcc tcagttcaaa attgattcaa actaacagtt       60
ccatgtcggg aaacagcacc aggaagctcg tgacatatgg tctttcattg cgagaaacat      120
cttacttatg tacatttcta agctatagcg tctacccttg tcagacccag gacgatgggt      180
gtcacatctc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccta ttagggcaag cggtgccagt agcagaatat      360
gtcacctcaa taactcgatc caccctgcc cattacatgg gtaacatatc catggaggtt      420
cgatgtatac tcgaggatac agtcgtccat cacgcccgcc tacatacca ttacatcagc      480 atag                                                                  484

<210> SEQ ID NO 4
<211> LENGTH: 484
<212> TYPE: DNA
<213> ORGANISM: Propionibacterium acnes

<400> SEQUENCE: 4
gttgcacacc agggggtcaa cttggcgtcc tcagttcaaa attgattcaa actaacagtt       60
ccatgtcggg aaacagcacc aggaagctcg tgacatatgg tctttcattg cgagaaacat      120
cttacttatg tacatttcta agctatagcg tctacccttg tcagacccag gacgatgggt      180
gtcacatctc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccta ttagggcaag cggtgccagt agcagaatat      360
gtcacctcaa caactcgatc caccctgcc cattacatgg gtaacatatc catggaggtt      420
cgatgtatac tcgaggatac agtcgtccat cacgcccgcc tacatacca ttacatcagc      480 atag                                                                  484

<210> SEQ ID NO 5
<211> LENGTH: 484
<212> TYPE: DNA
<213> ORGANISM: Propionibacterium acnes

<400> SEQUENCE: 5
gttgcacacc agggggtcaa cttggcgtcc tcagttcaaa attgattcaa actaacagtt       60
ccatgccggg aaacagcacc aggaagctcg tgacatatcg tctttcattg cgagaaacat      120
cttacttatg tacatttcta agctatagcg tctacccttg tcagacccag gacgatgggt      180
gtcacatctc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccta ttagggcaag cggtgccagt agcagaatat      360
gtcacctcaa caactcgatc caccctgcc cattacatgg gtaacatatc catggaggtt      420
cgatgtatac tcgaggatac agtcgtccat cacgcccgcc tacatacca ttacatcagc      480 atag                                                                  484
```

```
<210> SEQ ID NO 6
<211> LENGTH: 484
<212> TYPE: DNA
<213> ORGANISM: Propionibacterium acnes

<400> SEQUENCE: 6
gttgcacacc agggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgccctta ttagggcaag cggtgccagt agcagaatat     360
gtcacctcaa caactcgatc cacccctgcc cattacatgg gtaacatatc catggaggtt     420
cgatgtatac tcgaggatac agtcgtccat cacgcccgcc tacataccca ttacatcagc     480
atat                                                                  484

<210> SEQ ID NO 7
<211> LENGTH: 484
<212> TYPE: DNA
<213> ORGANISM: Propionibacterium acnes

<400> SEQUENCE: 7
gttgcacacc aggggggtcaa cttggcgtcc tcagttcaaa attgattcaa actaacagtt     60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgccatcac gaaggccacc acaatctatc ccagaacagc cggcacttca ctcacgatgc    300
cccgattctg gattcctatt gtcgccctta ttagggcaag cggtgccagt agcagaatat    360
gtcacctcaa caactcgatc cacccctgcc cattacatgg gtaacatatc catggaggtt    420
cgatgtatac tcgaggatac agtcgtccat cacgcccgcc tacataccca ttacatcagc    480
atag                                                                  484

<210> SEQ ID NO 8
<211> LENGTH: 484
<212> TYPE: DNA
<213> ORGANISM: Propionibacterium acnes

<400> SEQUENCE: 8
gttgcacacc aggggggtcaa cttggcgtcc tcagttcaaa attgattcaa actaacagtt     60
ccatgtcggg aaacagcacc aggaagctcg tgacatatcg cctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc cacccctgcc cattacatgg gtaacatatc catggaggtt    420
cgatgtatac tcgaggatac agtcgtccat cacgcccgcc tacataccca ttacatcagc    480
atag                                                                  484

<210> SEQ ID NO 9
```

```
<211> LENGTH: 484
<212> TYPE: DNA
<213> ORGANISM: Propionibacterium acnes

<400> SEQUENCE: 9
gttgcacacc aggggtcaa cttggcgtcc tcagttcaaa attgattcaa actaacagtt        60
ccatgccggg aaacagcacc aggaagctcg tgacatatcg tctttcattg cgagaaacat       120
cttacttatg tacatttcta agctatagcg tctacccttg tcagacccag gacgatgggt       180
gtcacatctc ctttctagtc aacctaagag aggaggaaat gccgcgatat atgttccacc       240
ctgtcatcat gaaggccacc acaatctatc ccagaacagc cggcacttca ctcacgatgc       300
cccgatgctg gattcctatt gtcgcccttda ttagggcaag cggtgccagt agcagaatat      360
gtcacctcaa caactcgatc cacccctgcc cattacatgg gtaacatatc catggaggtt       420
cgatgtatac tcgaggatac agtcgtccat cacgcccgcc tacatacccca ttacatcagc     480 atag                                                                    484

<210> SEQ ID NO 10
<211> LENGTH: 484
<212> TYPE: DNA
<213> ORGANISM: Propionibacterium acnes

<400> SEQUENCE: 10
gttgcacacc aggggtcaa cttggcgtcc tcagttcaaa attgattcaa actaacagtt        60
ccatgccggg aaacagcacc aggaagctcg tgacatatcg tctttcattg cgagaaacat       120
cttacttatg tacatttcta agctatagcg tctacccttg tcagacccag gacgatgggt       180
gtcacatctc ctttctagtc aacctaagag aggaggaaat gccgcgatat atgttccacc       240
ctgtcatcac gaaggccacc acaatctatc ccagaacagc cggcacttca ctcacgatgc       300
cccgatgctg gattcctatt gtcgcccttda ttagggcaag cggtgccagt agcagaatat      360
gtcacctcaa caactcgatc tacccctgcc cattacatgg gtaacatatc catggaggtt       420
cgatgtatac tcgaggatac agtcgtccat cacgcccgcc tacatacccca ttacatcagc     480 atag                                                                    484

<210> SEQ ID NO 11
<211> LENGTH: 484
<212> TYPE: DNA
<213> ORGANISM: Propionibacterium acnes

<400> SEQUENCE: 11
gttgcacacc aggggtcaa cttggcgtcc tcagttcaaa attgattcaa actaacagtt        60
ccatgccggg aaacagcacc aggaagcccg tgacatatcg tctttcattg cgagaaacat       120
cttacttatg tacatttcta agctatagcg tctacccttg tcagacccag gacgatgggt       180
gtcacatctc ctttctagtc aacctaagag aggaggaaat gccgcgatat atgttccacc       240
ctgtcatcac gaaggccacc acaatctatc ccagaacagc cggcacttca ctcacgatgc       300
cccgatgctg gattcctatt gtcgcccttda ttagggcaag cggtgccagt agcagaatat      360
gtcacctcaa caactcgatc cacccctgcc cattacatgg gtaacatatc catggaggtt       420
cgatgtatac tcgaggatac agtcgtccat cacgcccgcc tacatacccca ttacatcagc     480 atag                                                                    484

<210> SEQ ID NO 12
<211> LENGTH: 484
```

```
<212> TYPE: DNA
<213> ORGANISM: Propionibacterium acnes

<400> SEQUENCE: 12
gttgcacacc agggggtcaa cttggcgtcc tcagttcaaa attgattcaa actaacagtt         60
ccatgccggg aaacagcacc aggaagctcg tgacatatcg tctttcattg cgagaaacat        120
cttacttatg tacatttcta agctatagcg tctacccttg tcagacccag gacgatgggt        180
gtcacatctc ctttctagtc aacctaagag aggaggaaat gccgcgatat atattccacc        240
ctgtcatcac gaaggccacc acaatctatc ccagaacagc cggcacttca ctcacgatgc        300
cccgatgctg gattcctatt gtcgccctta ttagggcaag cggtgccagt agcagaatat        360
gtcacctcaa caactcgatc cacccctgcc cattacatgg gtaacatatc catggaggtt        420
cgatgtatac tcgaggatac agtcgtccat cacgcccgcc tacataccca ttacatcagc        480
atag                                                                      484

<210> SEQ ID NO 13
<211> LENGTH: 484
<212> TYPE: DNA
<213> ORGANISM: Propionibacterium acnes

<400> SEQUENCE: 13
gttgcacacc agggggtcaa cttggcgtcc tcagttcaaa attgattcaa actaacagtt         60
ccatgtcggg aaacagcacc aggaagctgg tgacatatcg tctttcattg cgagaaacat        120
cttacttatg tacatttcta agctatagcg tctacccttg tcagacccag gacgatgggt        180
gtcacatctc ctttctagtc aacctaagag aggaggaaat gccgcgatat atgttccacc        240
ctgtcatcac gaaggccacc acaatctatc ccagaacagc cggcacttca ctcacgatgc        300
cccgatgctg gattcctatt gtcgccctta ttagggcaag cggtgccagt agcagaatat        360
gtcacctcaa caactcgatc cacccctgcc cattacatgg gtaacatatc catggaggtt        420
cgatgtatac tcgaggatac agtcgtccat cacgcccgcc tacataccca ttacatcagc        480
atag                                                                      484

<210> SEQ ID NO 14
<211> LENGTH: 484
<212> TYPE: DNA
<213> ORGANISM: Propionibacterium acnes

<400> SEQUENCE: 14
gttgcacacc agggggtcaa cttggcgttt tcagttcaaa attgattcaa actaacagtt         60
ccatgccggg aaacagcacc aggaagctcg tgacatatcg tctttcattg cgagaaacat        120
cttacttatg tacatttcta agctatagcg tctacccttg tcagacccag gacgatgggt        180
gtcacatctc ctttctagtc aacctaagag aggaggaaat gccgcgatat atgttccacc        240
ctgtcatcac gaaggccacc acaatctatc ccagaacagc cggcacttca ctcacgatgc        300
cccgatgctg gattcctatt gtcgccctta ttagggcaag cggtgccagt agcagaatat        360
gtcacctcaa caactcgatc cacccctgcc cattacatgg gtaacatatc catggaggtt        420
cgatgtatac tcgaggatac agtcgtccat cacgcccgcc tacataccca ttacatcagc        480
atag                                                                      484

<210> SEQ ID NO 15
<211> LENGTH: 484
<212> TYPE: DNA
```

<213> ORGANISM: Propionibacterium acnes

<400> SEQUENCE: 15
gttgcacacc agggggtcaa cttggcgtcc tcagttcaaa attgattcaa actaacagtt      60
ccatgccggg aaacagtacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgccctta ttagggcaag cggtgccagt agcagaatat     360
gtcacctcaa caactcgatc cacccctgcc cattacatgg gtaacatatc catggaggtt     420
cgatgtatac tcgaggatac agtcgtccat cacgcccgcc tacatacccca ttacatcagc     480 atag                                                                   484

<210> SEQ ID NO 16
<211> LENGTH: 484
<212> TYPE: DNA
<213> ORGANISM: Propionibacterium acnes

<400> SEQUENCE: 16
gttgcacacc agggggtcaa cttggcgtcc tcagttcaaa attgattcaa actaacagtt      60
ccatgccggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gatccctatt gtcgccctta ttagggcaag cggtgccagt agcagaatat     360
gtcacctcaa caactcgatc cacccctgcc cattacatgg gtaacatatc catggaggtt     420
cgatgtatac tcgaggatac agtcgtccat cacgcccgcc tacatacccca ttacatcagc     480 atag                                                                   484

<210> SEQ ID NO 17
<211> LENGTH: 484
<212> TYPE: DNA
<213> ORGANISM: Propionibacterium acnes

<400> SEQUENCE: 17
gttgcacacc agggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgccctta ttagggcaag cggtgccggt agcagaatat     360
gtcacctcaa caactcgatc cacccctgcc cattacatgg gtaacatatc catggaggtt     420
cgatgtatac tcgaggatac agtcgtccat cacgcccgcc tacatacccca ttacatcagc     480 atag                                                                   484

<210> SEQ ID NO 18
<211> LENGTH: 484
<212> TYPE: DNA
<213> ORGANISM: Propionibacterium acnes -continued

<400> SEQUENCE: 18

```
gttgcacacc agggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgccctta ttagggcaag cggtgccagt agcagaatat     360
gccacctcaa caactcgatc cacccctgcc cattacatgg gtaacatatc catggaggtt     420
cgatgtatac tcgaggatac agtcgtccat cacgcccgcc tacataccca ttacatcagc     480
atag                                                                  484
```

<210> SEQ ID NO 19
<211> LENGTH: 484
<212> TYPE: DNA
<213> ORGANISM: Propionibacterium acnes

<400> SEQUENCE: 19

```
gttgcacacc agggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt gtcgccctta ttagggcaag cggtgccagt agcagaatat     360
gtcacctcaa caactcgatc gaccoctgcc cattacatgg gtaacatatc catggaggtt     420
cgatgtatac tcgaggatac agtcgtccat cacgcccgcc tacataccca ttacatcagc     480
atag                                                                  484
```

<210> SEQ ID NO 20
<211> LENGTH: 484
<212> TYPE: DNA
<213> ORGANISM: Propionibacterium acnes

<400> SEQUENCE: 20

```
gttgcacacc agggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatctc ctttctagtc aacctaagag aggaggaaat gccgcgatat atgttccacc     240
ctgtcatcac gaaggccacc acaatctatc ccagaacagc cggcacttca ctcacgatgc     300
cccgatgctg gattcctatt ttcgccctta ttagggcaag cggtgccagt agcagaatat     360
gtcacctcaa caactcgatc cacccctgcc cattacatgg gtaacatatc catggaggtt     420
cgatgtatac tcgaggatac agtcgtccat cacgcccgcc tacataccca ttacatcagc     480
atag                                                                  484
```

<210> SEQ ID NO 21
<211> LENGTH: 484
<212> TYPE: DNA
<213> ORGANISM: Propionibacterium acnes -continued

```
<400> SEQUENCE: 21
gttgcacacc aggggggtcaa cttggcgtcc tcagttcaaa attgattcaa actaacagtt       60
ccatgccggg aaacagcacc aggaagctcg tgacatatcg tctttcattg cgagaaacat      120
cttacttatg tacatttcta agctatagcg tctaccccttg tcagacccag gacgatgggt      180
gtcacatctc ctttctagtc aacctaagag aggaggaaat gccgcgatat atgttccacc      240
ctgtcatcac gaaggccacc acaatctatc ccagaacagc cggcacttca ctcacaatgc      300
cccgatgctg gattcctatt gtcgcccttg ttagggcaag cggtgccagt agcagaatat      360
gtcacctcaa caactcgatc caccccctgcc cattacatgg gtaacatatc catggaggtt      420
cgatgtatac tcgaggatac agtcgtccat cacgcccgcc tacatacccca ttacatcagc      480 atag                                                                   484

<210> SEQ ID NO 22
<211> LENGTH: 484
<212> TYPE: DNA
<213> ORGANISM: Propionibacterium acnes

<400> SEQUENCE: 22
gttgcacacc aggggggtcaa cttggcgtcc tcagttcaaa attgattcaa actaacagtt       60
ccatgccggg aaacagcacc aggaagctcg tgacatatcg tctttcattg cgagaaacat      120
cttacttatg tacatttcta agctatagcg tctaccccttg tcagacccag gacgatgggt      180
gtcacatctc ctttctggtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccttg ttagggcaag cggtgccagt agcagaatat      360
gtcacctcaa caactcgatc caccccctgcc cattacatgg gtaacatatc catggaggtt      420
cgatgtatac tcgaggatac agtcgtccat cacgcccgcc tacatacccca ttacatcagc      480 atag                                                                   484

<210> SEQ ID NO 23
<211> LENGTH: 484
<212> TYPE: DNA
<213> ORGANISM: Propionibacterium acnes

<400> SEQUENCE: 23
gttgcacacc aggggggtcaa cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatagcg tctaccccttg tcagacccag gacgatgggt      180
gtcacatctc ctttctagtc aacccaagag aggaggaaat gccgcgatat atgttccacc      240
ctgtcatcac gaaggccacc acaatctatc ccagaacagc cggcacttca ctcacgatgc      300
cccgattctg gattcctatt gtcgcccttg ttagggcaag cggtgccagt agcagaatat      360
gtcacctcaa caactcgatc caccccctgcc cattacatgg gtaacatatc catggaggtt      420
cgatgtatac tcgaggatac agtcgtccat cacgcccgcc tacatacccca ttacatcagc      480 atag                                                                   484

<210> SEQ ID NO 24
<211> LENGTH: 484
<212> TYPE: DNA
<213> ORGANISM: Propionibacterium acnes

<400> SEQUENCE: 24
```

-continued gttgcacacc agggggtcaa cttggcgtcc tcagttcaaa attgattcaa actaacagtt        60
ccatgtcggg aaacagcacc aggaagctcg tgacatatcg tctttcattg cgagaaacat       120
cttacttatg tacatttcta agctatagcg tctacccttg tcagacccag gacgatgggt       180
gtcacatccc ctttctagtc aacctaagag aggaggaaat gccgcgatat atgttccacc       240
ctgtcatcac gaaggccacc acaatctatc ccagaacagc cggcacttca ctcacgatgc       300
cccgatgctg gattcctatt gtcgcccta ttagggcaag cggtgccagt agcagaatat       360
gtcacctcag caactcgatc cacccctgcc cattacatgg gtaacatatc catggaggtt       420
cgatgtatac tcgaggatac agtcgtccat cacgcccgcc tacatacccca ttacatcagc       480 atag                                                                    484

<210> SEQ ID NO 25
<211> LENGTH: 484
<212> TYPE: DNA
<213> ORGANISM: Propionibacterium acnes

<400> SEQUENCE: 25
gttgcacacc agggggtcaa cttggcgtcc tcagttcaaa attgattcaa actaacagtt        60
ccatgtcggg aaacagcacc aggaagctcg tgacatatcg tctttcattg cgagaaacat       120
cttacttatg tacatttcta agctatagcg tctacccttg tcagacccag gacgatgggt       180
gtcacatccc ctttctagtc aacctaagag aggaggaaat gccgcgatat atgttccacc       240
ctgtcatcac gaaggccacc acaatctatc ccagaacagc cggcacttca ctcacgatgc       300
cccgatgctg gattcctatt gtcgcccta ttagggcaag cggtgccagt agcagaatat       360
gtcacctcaa caactcgatc cacccctgcc cattacatgg gtaacatatc catggaggtt       420
cgatgtatac tcgaggatac agtcgtccat cacgcccgcc tacatacccca ttacatcagc       480 atag                                                                    484

<210> SEQ ID NO 26
<211> LENGTH: 484
<212> TYPE: DNA
<213> ORGANISM: Propionibacterium acnes

<400> SEQUENCE: 26
gttgcacacc agggggtcaa cttggcgtcc tcagttcaaa attgattcaa actaacagtt        60
ccatgtcggg aaacagcacc aggaagctcg tgacatatcg tctttcattg cgagaaacat       120
cttacttatg tacatttcta agctatagcg tctacccttg tcagacccat gacgatgggt       180
gtcacatccc ctttctagtc aacctaagag aggaggaaat gccgcgatat atgttccacc       240
ctgtcatcac gaaggccacc acaatctatc ccagaacagc cggcacttca ctcacgatgc       300
cccgatgctg gattcctatt gtcgcccta ttagggcaag cggtgccagt agcagaatat       360
gtcacctcaa caactcgatc cacccctgcc cattacatgg gtaacatatc catggaggtt       420
cgatgtatac tcgaggatac agtcgtccat cacgcccgcc tacatacccca ttacatcagc       480 atag                                                                    484

<210> SEQ ID NO 27
<211> LENGTH: 484
<212> TYPE: DNA
<213> ORGANISM: Propionibacterium acnes

<400> SEQUENCE: 27

-continued

```
gttgcacacc aggggggtcaa cttggcgtcc ttagttcaaa attgattcaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatgggt      180
gtcacatccc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccta ttagggcaag cggtgccagt agcagaatat      360
gtcacctcaa caactcgatc cacccctgcc cattacatgg gtaacatatc catggaggtt      420
cgatgtatac tcgaggatac agtcgtccat cacgcccgcc tacatacccca ttacatcagc      480 atag                                                                   484
```

```
<210> SEQ ID NO 28
<211> LENGTH: 484
<212> TYPE: DNA
<213> ORGANISM: Propionibacterium acnes

<400> SEQUENCE: 28
gttgcacacc aggggggtcaa cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatgggt      180
gtcacatccc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccta ttagggcaag cggtgccagt agcagaatat      360
gtcacctcaa caactcgatc cacccctgcc cattacatgg gtaacatatc catggaggtt      420
cgatgtatac tcgaggatac agtcgtccat cacgcccgcc tacatacccca ttacatctgc      480 atag                                                                   484
```

```
<210> SEQ ID NO 29
<211> LENGTH: 484
<212> TYPE: DNA
<213> ORGANISM: Propionibacterium acnes

<400> SEQUENCE: 29
gttgcacacc aggggggtcaa cttggcgtcc tcagttcaaa attgattcaa actaacagtt       60
ccatgtcggg aaacagcacc aggaaactcg tgacatatcg tctttcattg cgagaaacat      120
cttacttatg tacatttcta agctatagcg tctacccttg tcagacccag gacgatgggt      180
gtcacatccc ctttctagtc aacctaagag aggaggaaat gccgcgatat atgttccgcc      240
ctgtcatcac gaagaccacc acaatctatc ccagaacagc cggcacttca ctcacgatgc      300
cccgatgctg gattcctatt gtcgcccta ttagggcaag cggtgccagt agcagaatat      360
gtcacctcaa caactcgatc cacccctgcc cattacatgg gtaacatatc catggaggtt      420
cgatgtatac ttgaggatac agtcgtccat cacgcccacc tacatacccca ttacatcagc      480 atag                                                                   484
```

```
<210> SEQ ID NO 30
<211> LENGTH: 484
<212> TYPE: DNA
<213> ORGANISM: Propionibacterium acnes

<400> SEQUENCE: 30
gttgcacacc aggggggtcaa cttggcgtcc tcagttcaaa attgattcaa actaacagtt       60
```

```
ccatgtcggg aaacagcacc aggaaactcg tgacatatcg tctttcattg cgagaaacat      120
cttacttatg tacatttcta agctatagcg tctacccttg tcagacccag gacgatgggt      180
gtcacatccc ctttctagtc aacctaagag aggaggaaac gccgcgatat atgttccgcc      240
ctgtcatcac gaagaccacc acaatctatc ccagaacagc cggcacttca ctcacgatgc      300
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatac ttgaggatac agtcgtccat cacgcccacc tacatacccca ttacatcagc     480 atag                                                                   484

<210> SEQ ID NO 31
<211> LENGTH: 484
<212> TYPE: DNA
<213> ORGANISM: Propionibacterium acnes

<400> SEQUENCE: 31
gttgcacacc aggggtcaa cttggcgtcc tcagttcaaa attgattcaa actaacagtt       60
ccatgtcggg aaacagcacc aggaaactcg tgacatatcg tctttcattg cgagaaacat      120
cttacttatg tacatttcta agctatagcg tctacctttg tcagacccag gacgatgggt      180
gtcacatccc ctttctagtc aacctaagag aggaggaaat gccgcgatat atgttccgcc      240
ctgtcatcac gaagaccacc acaatctatc ccagaacagc cggcacttca ctcacgatgc      300
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatac ttgaggatac agtcgtccat cacgcccacc tacatacccca ttacatcagc     480 atag                                                                   484

<210> SEQ ID NO 32
<211> LENGTH: 484
<212> TYPE: DNA
<213> ORGANISM: Propionibacterium acnes

<400> SEQUENCE: 32
gttgcacacc aggggtcaa cttggcgtcc tcagttcaaa attgatttaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacctca ctcacgatgc      300
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatat tcgagaatac agtcgtccat cacgcccgcc tacatacccca ttacatcagc     480 atag                                                                   484

<210> SEQ ID NO 33
<211> LENGTH: 484
<212> TYPE: DNA
<213> ORGANISM: Propionibacterium acnes

<400> SEQUENCE: 33
gttgcacacc aggggtcaa cttggcgtcc tcagttcaaa attgatttaa actaacagtt       60
```

-continued

```
ccatgtcggg aaacagcacc agaaagctcg tgacatatcg tctttcattg cgagaaacat      120
cttacttatg tacatttcta agctatagcg tctacccttg tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacctca ctcacgatgc      300
cccgatgctg gattcctatt gtcgcccta ttagggcaag cggtgccagt agcagaatat       360
gtcacctcaa caactcgatc cacccctgcc cattacatgg gtaacatatc catggaggtt      420
cgatgtatat tcgaggatac agtcgtccat cacgcccgcc tacataccca ttacatcagc      480
atag                                                                   484

<210> SEQ ID NO 34
<211> LENGTH: 484
<212> TYPE: DNA
<213> ORGANISM: Propionibacterium acnes

<400> SEQUENCE: 34
gttgcacacc agggggtcaa cttggcgtcc tcagttcaaa attgatttaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacctca ctcacgatgc      300
cccgatgctg gattcctatt gtcgcccta ttagggcaag cggtgccagt agcagaatat       360
gtcacctcaa caactcgatc cacccctgcc cattacatgg gtaacatatc catggaggtt      420
cgatgtatat tcgaggatac agtcgtccat cacgcccgcc tacataccca ttacatcagc      480
atag                                                                   484

<210> SEQ ID NO 35
<211> LENGTH: 484
<212> TYPE: DNA
<213> ORGANISM: Propionibacterium acnes

<400> SEQUENCE: 35
gttgcacacc agggggtcaa cttggcgtcc tcagttcaaa attgatttaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacctca ctcacgatgc      300
cccgatgctg gattcctatt gtcgcccta ttagggcaag cggtgccagt agcagaatat       360
gtcacctcaa caactcgatc cacccctgcc cattacatgg gtaacatatc catgaaggtt      420
cgatgtatat tcgaggatac agtcgtccat cacgcccgcc tacataccca ttacatcagc      480
atag                                                                   484

<210> SEQ ID NO 36
<211> LENGTH: 484
<212> TYPE: DNA
<213> ORGANISM: Propionibacterium acnes

<400> SEQUENCE: 36
gttgcacacc agggggtcaa cttggcgtcc tcagttcaaa attgatttaa actaacagtt       60
tcatgtcggg aaacagcacc aggaagctcg tgacatatcg tctttcattg cgagaaacat      120
```

```
cttacttatg tacatttcta agctatagcg tctacccttg tcagacccag gacgatggat        180
gtcacatccc ctttctagtc aacctaagag aggaggaaat gccgcgatat atgttccacc        240
ctgtcatcac gaaggccacc acaatctatc ccagaacagc cggcacctca ctcacgatgc        300
cccgatgctg gattcctatt gtcgcccttat ttagggcaag cggtgccagt agcagaatat       360
gtcacctcaa caactcgatc caccc ctgcc cattacatgg gtaacatatc catggaggtt       420
cgatgtatat tcgaggatac agtcgtccat cacgcccgcc tacatacccca ttacatcagc       480 atag                                                                      484

<210> SEQ ID NO 37
<211> LENGTH: 484
<212> TYPE: DNA
<213> ORGANISM: Propionibacterium acnes

<400> SEQUENCE: 37
gttgcacacc aggggggtcaa cttggcgtcc tcagttcaaa attgatttaa actaacagtt         60
ccatgtcggg aaacagcacc aggaagctcg tgacatatcg tctttcattg cgagaaacat        120
cttacttatg tacatttcta agctatagcg tctacccttg tcagacccag gacgatggat        180
gtcacatccc ctttctagtc aacctaagag aggaggaaat tccgcgatat atgttccacc        240
ctgtcatcac gaaggccacc acaatctatc ccagaacagc cggcacctca ctcacgatgc        300
cccgatgctg gattcctatt gtcgcccttat ttagggcaag cggtgccagt agcagaatat       360
gtcacctcaa caactcgatc caccc ctgcc cattacatgg gtaacatatc catggaggtt       420
cgatgtatat tcgaggatac agtcgtccat cacgcccgcc tacatacccca ttacatcagc       480 atag                                                                      484

<210> SEQ ID NO 38
<211> LENGTH: 484
<212> TYPE: DNA
<213> ORGANISM: Propionibacterium acnes

<400> SEQUENCE: 38
gttgcacacc agagggtcaa cttggcgtcc tcagttcaaa attgatttaa actaacagtt          60
ccatgtcggg aaacagcacc aggaagctcg tgacatatcg tctttcattg cgagaaacat        120
cttacttatg tacatttcta agctatagcg tctaccttg tcagacccag gacgatggat         180
gtcacatccc ctttctagtc aacctaagag aggaggaaat gccgcgatat atgttccacc        240
ctgtcatcac gaaggccacc acaatctatc ccagaacagc cggcacctca ctcacgatgc        300
cccgatgctg gattcctatt gtcgcccttat ttagggcaag cggtgccagt agcagaatat       360
gtcacctcaa caactcgatc caccc ctgcc cattacatgg gtaacatatc catggaggtt       420
cgatgtatat tcgaggatac agtcgtccat cacgcccgcc tacatacccca ttacatcagc       480 atag                                                                      484

<210> SEQ ID NO 39
<211> LENGTH: 484
<212> TYPE: DNA
<213> ORGANISM: Propionibacterium acnes

<400> SEQUENCE: 39
gttgcacacc aggggggtcaa cttggcgtcc tcagttcaaa attgatttaa actaacagtt         60
ccatgtcggg aaacagcacc aggaagctcg tgacatatcg tctttcattg cgagaaacat        120
```

```
cttacttatg tacatttcta agctatagcg tctacccttg tcagacccag gacgatggat      180
gtcacatccc ctttctagtc aacctaagag aggaggaaat gccgcgatat atgttccacc      240
ctgtcatcac gaaggccacc acaatctatc ccagaacagc cggcgcctca ctcacgatgc      300
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatat tcgaggatac agtcgtccat cacgcccgcc tacatacccca ttacatcagc     480 atag                                                                   484

<210> SEQ ID NO 40
<211> LENGTH: 484
<212> TYPE: DNA
<213> ORGANISM: Propionibacterium acnes

<400> SEQUENCE: 40
gttgcacacc aggggggtcaa cttggcgtcc tcagttcaaa atagatttaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacctca ctcacgatgc      300
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatat tcgaggatac agtcgtccat cacgcccgcc tacatacccca ttacatcagc     480 atag                                                                   484

<210> SEQ ID NO 41
<211> LENGTH: 484
<212> TYPE: DNA
<213> ORGANISM: Propionibacterium acnes

<400> SEQUENCE: 41
gttgcacacc aggggggtcaa cttggcgtcc tcagttcaaa attgattcaa actaacagtt       60
ccatgtcggg aaacagcacc aggaagctcg tgacatatcg tctttcattg cgagaaacat      120
cttacttatg tatatttcta agctatagcg tctacccttg tcagacccag gacgatgggt      180
gtcacatccc ctttctagtc aacctaagag aggaggaaat gccgcgatat atgttccacc      240
ctgtcatcac gaacgccacc acaatctatc ccagaacagc cggcacttca ctcacgatgc      300
cccgattctg gattcctatt gtcgccctta ttagggcaag cggtgccagt agcagaatat      360
gtcacctcaa caactcgatc cacccctgcc cattacatgg gtaacatatc catggaggtt      420
cgatgtatac tcgaggatac agtcgtccat cacgcccgcc tacatacccca ttacatcagc     480 atag                                                                   484

<210> SEQ ID NO 42
<211> LENGTH: 484
<212> TYPE: DNA
<213> ORGANISM: Propionibacterium acnes

<400> SEQUENCE: 42
gttgcacacc aggggggtcaa cttggcgtcc tcagttcaaa attgattcaa actaacagtt       60
ccatgtcggg aaacagcacc aggaagctcg tgacatatcg tctttcattg cgagaaacat      120
cttacttatg tatatttcta agctatagcg tctacccttg tcagacccag gacgatgggt      180
```

-continued

```
gtcacatccc ctttctagtc aacctaagag aggaggaaat gccgcgatat atgttccacc      240
ctgtcatcac gaacgccacc acaatctatc ccagaacagc cggcacttca ctcacgatgc      300
cccgattctg gattcctatt gtcgcccta ttagggcaag cggtgccagt agcagaatat       360
gtcacctcaa caactcgatc caccootgcc cattacatgg gtaacatatc catggaggtt      420
cgatgtatac tcgaggatac agtcgtccat cacgcccgcc tacatacccca ttacaccagc     480 atag                                                                   484

<210> SEQ ID NO 43
<211> LENGTH: 484
<212> TYPE: DNA
<213> ORGANISM: Propionibacterium acnes

<400> SEQUENCE: 43
gttgcacacc agggggtcaa cttggcgtcc tcagttcaaa attgattcaa actaacagtt       60
ccatgtcggg aaacagcacc aggaagctcg tgacatatcg tctttcattg cgagaaacat      120
cttacttatg tatatttcta agctatagcg tctacccttg tcagacccag gacgatgggt      180
gtcacatccc ctttctagtc aacctaagag aggaggaaat gccgcgatat atgttccacc      240
ctgtcatcac gaacgccacc acaatctatc ccagaacagc cggcacttca ctcacgatgc      300
cccgattctg gattcctatt gtcgcccta ttagggcaag cggtgccagt agcagaatat       360
gtcacctaaa caactcgatc caccootgcc cattacatgg gtaacatatc catggaggtt      420
cgatgtatac tcgaggatac agtcgtccat cacgcccgcc tacatacccca ttacatcagc     480 atag                                                                   484

<210> SEQ ID NO 44
<211> LENGTH: 484
<212> TYPE: DNA
<213> ORGANISM: Propionibacterium acnes

<400> SEQUENCE: 44
gttgcacacc agggggtcaa cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatgggt      180
gtcacatccc ctttctagtc aacctaagag aggaggaaat gccgcgatat atgttccacc      240
ctgtcatcac gaacgccacc acaatctatc ccagaacagc cggcacttca ctcacgatgc      300
cccgatgctg gattcctatt gtcgcccta ttagggcaag cggtgccagt agcagaatat       360
gtcacctcaa caactcgatc caccootgcc cattacatgg gtaacatatc catggaggtt      420
cgatgtatac tcgaggatac agtcgtccat cacgcccgcc tacatacccca ttacatcagc     480 atag                                                                   484

<210> SEQ ID NO 45
<211> LENGTH: 484
<212> TYPE: DNA
<213> ORGANISM: Propionibacterium acnes

<400> SEQUENCE: 45
gttgcacacc agggggtcaa cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatagcg tctacccttg tcagacccag gacgatgggt      180
```

-continued

```
gtcacatccc ctttctagtc aacctaagag aggaggaaat gccgcgatat atgttccacc       240
ctgtcatcac gaacgccacc acaatctatc ccagaacagc cggcacttca ctcacgatgc       300
cccgatgcta gattcctatt gtcgcccttc ttagggcaag cggtgccagt agcagaatat       360
gtcacctcaa caactcgatc cacccctgcc cattacatgg gtaacatatc catggaggtt       420
cgatgtatac tcgaggatac agtcgtccat cacgcccgcc tacataccca ttacatcagc       480
atag                                                                     484

<210> SEQ ID NO 46
<211> LENGTH: 484
<212> TYPE: DNA
<213> ORGANISM: Propionibacterium acnes

<400> SEQUENCE: 46
gttacacacc aggggggtcaa cttggcgtcc tcagttcaaa attgattcaa actaacagtt        60
ccatgtcggg aaacagcacc aggaagctcg tgacatatcg tctttcattg cgagaaacat       120
cttacttatg tacatttcta agctatagcg tctacccttg tcagacccag gacgatgggt       180
gtcacatccc ctttctagtc aacctaagag aggaggaaat gccgcgatat atgttccacc       240
ctgtcatcac gaacgccacc acaatctatc ccagaacagc cggcacttca ctcacgatgc       300
cccgatgctg gattcctatt gtcgcccttc ttagggcaag cggtgccagt agcagaatat       360
gtcacctcaa caactcgatc cacccctgcc cattacatgg gtaacatatc catggaggtt       420
cgatgtatac tcgaggatac agtcgtccat cacgcccgcc tacataccca ttacatcagc       480
atag                                                                     484

<210> SEQ ID NO 47
<211> LENGTH: 484
<212> TYPE: DNA
<213> ORGANISM: Propionibacterium acnes

<400> SEQUENCE: 47
gttgcacacc aggggggtcaa cttggcgtcc tcagttcaaa attgattcaa actaacagtt        60
ccatgtcggg aaacagcacc aggaagctcg tgacatatcg tctttcattg cgagaaacat       120
cttacttatg tatatttcta agctatagcg tctacccttg tcagacccag gacgatgggt       180
gtcacatccc ctttctagtc aacctaagag aggaggaaat gccgcgatat atgttccacc       240
ctgtcatcac gaacgccacc acaatctatc ccagaacagc cggcacttca ctcacgatgc       300
cccgattctg gattcctatt gtcgcccttc ttagggcaag cggtgccagt agcagaatat       360
gtcacctcaa caactcgatc cacccctgcc cattacatgg gtaacatatc catggaggtt       420
cgatgtatac tcgaggatac agtcgtccat caagcccgcc tacataccca ttacatcagc       480
atag                                                                     484

<210> SEQ ID NO 48
<211> LENGTH: 484
<212> TYPE: DNA
<213> ORGANISM: Propionibacterium acnes

<400> SEQUENCE: 48
gttgcacacc aggggggtcaa cttggcgtcc tcagttcaaa attgattcaa actaacagtt        60
ccatgtcgga aaacagcacc aggaagctcg tgacatatcg tctttcattg cgagaaacat       120
cttacttatg tacatttcta agctatagcg tctacccttg tcagacccag gacgatgggt       180
gtcacatccc ctttctagtc aacctaagag aggaggaaat gccgcgatat atgttccacc       240
```

-continued

```
ctgtcatcac gaacgccacc acaatctatc ccagaacagc cggcacttca ctcacgatgc     300
cccgatgctg gattcctatt gtcgcccttta ttagggcaag cggtgccagt agcagaatat     360
gtcacctcaa caactcgatc caccctgcc cattacatgg gtaacatatc catggaggtt      420
cgatgtatac tcgaggatac agtcgtccat cacgcccgcc tacatacccca ttacatcagc    480 atag                                                                   484

<210> SEQ ID NO 49
<211> LENGTH: 484
<212> TYPE: DNA
<213> ORGANISM: Propionibacterium acnes

<400> SEQUENCE: 49
gttgcacacc aggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacatccc ctttctagtc aacctaagag aggaggaaat gccgcgatat atgttccacc     240
ctgtcatcac gaacgccacc acaatctatc ccagaacagc cggcacttca ctcacgatgc     300
cccgatgctg gattcctatt gtcgcccttta ttagggcaag cgatgccagt agcagaatat     360
gtcacctcaa caactcgatc caccctgcc cattacatgg gtaacatatc catggaggtt      420
cgatgtatac tcgaggatac agtcgtccat cacgcccgcc tacatacccca ttacatcagc    480 atag                                                                   484

<210> SEQ ID NO 50
<211> LENGTH: 484
<212> TYPE: DNA
<213> ORGANISM: Propionibacterium acnes

<400> SEQUENCE: 50
gttgcacacc aggggtcaa cttggcgtcc tcagttcaaa attgattcaa actaacagtt      60
ccatgtcggg aaacagcacc aggaagctcg tgacatatcg tctttcattg cgagaaacat     120
cttacttatg tacatttcta agctatagcg tctacccttg tcagacccag gacgatgggt     180
gtcacacccc ctttctagtc aacctaagag aggaggaaat gccgcgatat atgttccacc     240
ctgtcatcac gaacgccacc acaatctatc ccagaacagc cggcacttca ctcacgatgc     300
cccgatgctg gattcctatt gtcgcccttta ttagggcaag cggtgccagt agcagaatat     360
gtcacctcaa caactcgatc caccctgcc cattacatgg gtaacatatc catggaggtt      420
cgatgtatac tcgaggatac agtcgtccat cacgcccgcc tacatacccca ttacatcagc    480 atag                                                                   484

<210> SEQ ID NO 51
<211> LENGTH: 484
<212> TYPE: DNA
<213> ORGANISM: Propionibacterium acnes

<400> SEQUENCE: 51
gttgcacacc aggggtcaa cttggcgtcc tcagttcaaa attgattcaa actaacagtt      60
ccatgtcggg aaacagcacc aggaagctcg tgacatatcg cctttcattg cgagaaacat     120
cttacttatg tacatttcta agctatagcg tctacccttg tcagacccag gacgatgggt     180
gtcacatccc ctttctagtc aacctaagag aggaggaaat gccgcgatat atgttccacc     240
```

-continued

```
ctgtcatcac gaacgccacc acaatcgatc ccagaacagc cggcacttca ctcacgatgc      300
cccgatgctg gattcctatt gtcgcccta  ttagggcaag cggtgccagt agcagaatat      360
gtcacctcaa caactcgatc caccctgcc  cattacatgg gtaacatatc catggaggtt      420
cgatgtatac tcgaggatac agtcgtccat cacgcccgcc tacatacca  ttacatcagc      480 atag                                                                   484

<210> SEQ ID NO 52
<211> LENGTH: 484
<212> TYPE: DNA
<213> ORGANISM: Propionibacterium acnes

<400> SEQUENCE: 52
gttgcacacc aggggtcaa  cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatatcg tctaccttg  tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccta  ttagggcaag cggtgccagt agcagaatat      360
gtcacctcaa caactcgatc caccctgcc  cattacatgg gtaacatatc catggaggtt      420
cgatgtatat tcgaggatac agtcgtccat cacgcccgcc tacatacca  ttacatcagc      480 atag                                                                   484

<210> SEQ ID NO 53
<211> LENGTH: 484
<212> TYPE: DNA
<213> ORGANISM: Propionibacterium acnes

<400> SEQUENCE: 53
gttgcacacc aggggtcaa  cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatatcg tctaccttg  tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgccctca ttagggcaag cggtgccagt agcagaatat      360
gtcacctcaa caactcgatc caccctgcc  cattacatgg gtaacatatc catggaggtt      420
cgatgtatat tcgaggatac agtcgtccat cacgcccgcc tacatacca  ttacatcagc      480 atag                                                                   484

<210> SEQ ID NO 54
<211> LENGTH: 484
<212> TYPE: DNA
<213> ORGANISM: Propionibacterium acnes

<400> SEQUENCE: 54
gttgcacacc aggggtcaa  cttggcgtcc tcagttcaaa attgattcaa actaacagtt       60
ccatgtcggg aaacagcacc aggaagctcg tgacatatcg tctttcattg cgagaaacat      120
cttacttatg tacatttcta agctatatcg tccaccttg  tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacttca ctcacgatgc      300
```

-continued

```
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatat tcgaggatac agtcgtccat cacgcccgcc tacatacccca ttacatcagc     480 atag                                                                   484

<210> SEQ ID NO 55
<211> LENGTH: 484
<212> TYPE: DNA
<213> ORGANISM: Propionibacterium acnes

<400> SEQUENCE: 55
gttgcacacc aggggggtcaa cttggcgtcc tcagttcaaa attgattcaa actaacagtt      60
ccatgtcggg aaacagcacc aggaagctcg tgacatatcg tctttcattg cgagaaacat      120
cttacttatg tacatttcta agctatatcg tctacccttg tcagacccgg gacgatggat      180
gtcacatccc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatat tcgaggatac agtcgtccat cacgcccgcc tacatacccca ttacatcagc     480 atag                                                                   484

<210> SEQ ID NO 56
<211> LENGTH: 484
<212> TYPE: DNA
<213> ORGANISM: Propionibacterium acnes

<400> SEQUENCE: 56
gttgcacacc aggggggtcaa cttggcgtcc tcagttcaaa attgattcaa actaacagtt      60
ccatgtcggg aaacagcacc aggaagctcg tgacatatcg tctttcattg cgagaaacat      120
cttacttatg tacatttcta agccatatcg tctacccttg tcagacccag gacgatggat      180
gtcacatccc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgccctta ttagggcaag cggtgccagt agcagaatat      360
gtcacctcaa caactcgatc cacccctgcc cattacatgg gtaacatatc catggaggtt      420
cgatgtatat tcgaggatac agtcgtccat cacgcccgcc tacatacccca ttacatcagc     480 atag                                                                   484

<210> SEQ ID NO 57
<211> LENGTH: 484
<212> TYPE: DNA
<213> ORGANISM: Propionibacterium acnes

<400> SEQUENCE: 57
gttgcacacc aggggggtcaa cttggtgtcc tcagttcaaa attgattcaa actaacggtt      60
ccgtgtcggg aaacagcacc agaaaactcg tgacatatcg tctttcattg cgagaaacat      120
cttacttata cacatttcta agctatattg tctacccctg tcagacccag gacgatgggt      180
gtcatatccc ctttccagtc aacctaagaa gggaggaaat gccgcgatat atgttccgcc      240
ctgtcatcat gaatgccacc acaatctatc ccggaacagc cgtacttcac ccaccatgcc      300
```

-continued

```
ccgatgctgg attcctattg tcgcccttat tagagcaagc ggtgccagca gcagaatatt     360
tcacctcagc aactcgatcc gctcctgccc attacatggg taacatatcc atggaggtac     420
gatgtatgca tcgaggatgc agtcgtctac tatgcccgcc tacatacccà ttccatcagc     480 atag                                                                  484

<210> SEQ ID NO 58
<211> LENGTH: 484
<212> TYPE: DNA
<213> ORGANISM: Propionibacterium acnes

<400> SEQUENCE: 58
gttgcacacc aggggtcaa cttggtgtcc tcagttcaaa attggttcaa actaacggtt       60
ccgtgtcggg aaacagcacc agaaaactcg tgacatatcg tctttcattg cgagaaacat      120
cttacttata cacatttcta agctatattg tctaccctg tcagacccag gacgatgggt      180
gtcatatccc ctttccagtc aacctaagaa gggaggaaat gccgcgatat atgttccgcc     240
ctgtcatcat gaatgccacc acaatctatc ccggaacagc cgtacttcac ccaccatgcc     300
ccgatgctgg attcctattg tcgcccttat tagagcaagc ggtgccagca gcagaatatt     360
tcacctcagc aactcgatcc gctcctgccc attacatggg taacatatcc atggaggtac     420
gatgtatgca tcgaggatgc agtcgtctac tatgcccgcc tacatacccà ttccatcagc     480 atag                                                                  484

<210> SEQ ID NO 59
<211> LENGTH: 483
<212> TYPE: DNA
<213> ORGANISM: Propionibacterium acnes

<400> SEQUENCE: 59
gttgcacacc aggggtcaa cttggtgtcc tcagttcaaa attgattcaa actaacggtt       60
ccgtgtcggg aaacagcacc agaaaactcg tgacatatcg tctttcattg cgagaaacat      120
cttacttata cacatttcta agctatatgt ctaccctgt cagacccagg acgatgggtg      180
tcatatcccc tttccagtca acctaagaag ggaggaaatg ccgcgatata tgttccgccc     240
tgtcatcatg aatgccacca caatctatcc cggaacagcc gtacttcacc caccatgccc     300
cgatgctgga ttcctattgt cgcccttatt agagcaagcg gtgccagcag cagaatattt     360
cacctcagca actcgatccg ctcctgccca ttacatgggt aacatatcca tggaggtacg     420
atgtatgcat cgaggatgca gtcgtctact atgcccgcct acatacccat tccatcagca     480
tag                                                                   483

<210> SEQ ID NO 60
<211> LENGTH: 484
<212> TYPE: DNA
<213> ORGANISM: Propionibacterium acnes

<400> SEQUENCE: 60
gttgcacacc aggggtcaa cttggtgtcc tcagttcaaa attgattcaa actaacggtt       60
ccgtgtcggg aaacagcacc agaaaactcg taacatatcg tctttcattg cgagaaacat      120
cttacttata cacatttcta agctatattg tctaccctg tcagacccag gacgatgggt      180
gtcatatccc ctttccagtc aacctaagaa gggaggaaat gccgcgatat atgttccgcc     240
ctgtcatcat gaatgccacc acaatctatc ccggaacagc cgtacttcac ccaccatgcc     300
ccgatgctgg attcctattg tcgcccttat tagagcaagc ggtgccagca gcagaatatt     360
```

-continued

```
tcacctcagc aactcgatcc gctcctgccc attacatggg taacatatcc atggaggtac     420
gatgtatgca tcgaggatgc agtcgtctac tatgcccgcc tacataccca ttccatcagc     480
atag                                                                  484

<210> SEQ ID NO 61
<211> LENGTH: 484
<212> TYPE: DNA
<213> ORGANISM: Propionibacterium acnes

<400> SEQUENCE: 61
gttgcacacc agggggtcaa cttggtgtcc tcagttcaaa attgattcaa actaacggtt      60
ccgtgtcggg aaacagcacc agaaaactcg tgacatatcg tctttcattg cgagaaacat     120
cttacttata cacatttcta agctatattg tctacccctg tcagacccag gacgatgggt     180
gtcatatccc ctttccagtc aacctaagaa gggaggaaat gccgcgatat atgttccgcc     240
ctgtcatcat gaatgccacc acaatctatc ccggaacagc cgtacttcac ccaccatgcc     300
tcgatgctgg attcctattg tcgcccttat tagagcaagc ggtgccagca gcagaatatt     360
tcacctcagc aactcgatcc gctcctgccc attacatggg taacatatcc atggaggtac     420
gatgtatgca tcgaggatgc agtcgtctac tatgcccgcc tacataccca ttccatcagc     480
atag                                                                  484

<210> SEQ ID NO 62
<211> LENGTH: 484
<212> TYPE: DNA
<213> ORGANISM: Propionibacterium acnes

<400> SEQUENCE: 62
gttgcacacc agggggtcaa cttggtgtcc tcagttcaaa attgattcaa actaacggtt      60
ccgtgtcggg aaacagcacc agaaaactcg tgacatatcg tctttcattg cgagaaacat     120
cttatttata cacatttcta agctatattg tctacccctg tcagacccag gacgatgggt     180
gtcatatccc ctttccagtc aacctaagaa gggaggaaat gccgcgatat atgttccgcc     240
ctgtcatcat gaatgccacc acaatctatc ccggaacagc cgtacttcac ccaccatgcc     300
ccgatgctgg attcctattg tcgcccttat tagagcaagc ggtgccagca gcagaatatt     360
tcacctcagc aactcgatcc gctcctgccc attacatggg taacatatcc atggaggtac     420
gatgtatgca tcgaggatgc agtcgtctac tatgcccgcc tacataccca ttccatcagc     480
atag                                                                  484

<210> SEQ ID NO 63
<211> LENGTH: 484
<212> TYPE: DNA
<213> ORGANISM: Propionibacterium acnes

<400> SEQUENCE: 63
gttgcacacc agggggtcaa cttggtgtcc tcagttcaaa attgattcaa actaacggtt      60
ccgtgtcggg aaacagcacc agaaaactcg tgacatatcg tctttcattg cgagaaacat     120
cttacttata cacatttcta agctatattg tctacccctg tcagacccag gacgatgggt     180
gtcatatccc ctttccagtc aacctaagaa ggaaggaaat gccgcgatat atgttccgcc     240
ctgtcatcat gaatgccacc acaatctatc ccggaacagc cgtacttcac ccaccatgcc     300
ccgatgctgg attcctattg tcgcccttat tagagcaagc ggtgccagca gcagaatatt     360
```

-continued

```
tcacctcagc aactcgatcc gctcctgccc attacatggt taacatatcc atggaggtac     420
gatgtatgca tcgaggatgc agtcgtctac tatgcccgcc tacatacccca ttccatcagc     480 atag                                                                   484
```

```
<210> SEQ ID NO 64
<211> LENGTH: 484
<212> TYPE: DNA
<213> ORGANISM: Propionibacterium acnes

<400> SEQUENCE: 64
attgcacacc aggggggtcaa cttggtgtcc tcagttcaaa attggttcaa actaacggtt      60
ccgtgtcggg aaacagcacc agaaaactcg tgacatatcg tctttcattg cgagaaacat     120
cttacttata cacatttcta agctatattg tctacccctg tcagacccag gacgatgggt     180
gtcatatccc ctttccagtc aacctaagaa gggaggaaat gccgcgatat atgttccgcc     240
ctgtcatcat gaatgccacc acaatctatc ccggaacagc cgtacttcac ccaccatgcc     300
ccgatgctgg attcctattg tcgcccttat tagagcaagc ggtgccagca gcagaatatt     360
tcacctcagc aactcgatcc gctcctgccc attacatggg taacatatcc atggaggtac     420
gatgtatgca tcgaggatgc agtcgtctac tatgcccgcc tacatacccca ttccatcagc     480 atag                                                                   484
```

```
<210> SEQ ID NO 65
<211> LENGTH: 484
<212> TYPE: DNA
<213> ORGANISM: Propionibacterium acnes

<400> SEQUENCE: 65
gttgcacacc aggggggtcaa cttggtgtcc tcagttcaaa attggttcaa actaacggtt      60
ccgtgtcggg aaacagcacc agaaaactcg tgacatatcg tctttcattg cgagaaacat     120
cttacttata cacatttcta agctatattg tctacccctg tcagacccag gacgatgggt     180
gtcatatccc ctttccagtc aacctaagaa gggaggaaat gccgcgatat atgttccgcc     240
ctgtcatcat gaatgccacc acaatctatc ccggaacagc cgtacttcac ccaccatgcc     300
ccgatgctgg attcctatgg tcgcccttat tagagcaagc ggtgccagca gcagaatatt     360
tcacctcagc aactcgatcc gctcctgccc attacatggg taacatatcc atggaggtac     420
gatgtatgca tcgaggatgc agtcgtctac tatgcccgcc tacatacccca ttccatcagc     480 atag                                                                   484
```

```
<210> SEQ ID NO 66
<211> LENGTH: 483
<212> TYPE: DNA
<213> ORGANISM: Propionibacterium acnes

<400> SEQUENCE: 66
gttgcacacc aggggggtcaa cttggtgtcc tcagttcaaa attgattcaa actaacggtt      60
ccgtgtcggg aaacagcacc agaaaactcg tgacatatca tctttcattg cgagaaacat     120
cttacttata cacatttcta agctatatgt ctaccctgt cagacccagg acgatgggtg      180
tcatatcccc tttccagtca acctaagaag ggaggaaatg ccgcgatata tgttccgccc     240
tgtcatcatg aatgccacca caatctatc ccggaacagc cgtacttcac ccaccatgccc     300 cgatgctgga ttcctattgt cgcccttatt agagcaagcg gtgccagcag cagaatattt     360
cacctcagca actcgatccg ctcctgccca ttacatgggt aacatatcca tggaggtacg     420
```

-continued

```
atgtatgcat cgaggatgca gtcgtctact atgcccgcct acatacccat tccatcagca      480
tag                                                                     483

<210> SEQ ID NO 67
<211> LENGTH: 484
<212> TYPE: DNA
<213> ORGANISM: Propionibacterium acnes

<400> SEQUENCE: 67
gttgcacacc aggggtcaa cttggtgtcc tcagttcaaa attggttcaa actaacggtt        60
ccgtgtcggg aaacagcacc agaaaactcg tgacatgtcg tctttcattg cgagaaacat       120
cttacttata cacatttcta agctatattg tctacccctg tcagacccag gacgatgggt       180
gtcatatccc ctttccagtc aacctaagaa gggaggaaat gccgcgatat atgttccgcc       240
ctgtcatcat gaatgccacc acaatctatc ccggaacagc cgtacttcac ccaccatgcc       300
ccgatgctgg attcctattg tcgcccttat tagagcaagc ggtgccagca gcagaatatt       360
tcacctcagc aactcgatcc gctcctgccc attacatggg taacatatcc atggaggtac       420
gatgtatgca tcgaggatgc agtcgtctac tatgcccgcc tacatacccc ttccatcagc       480
atag                                                                    484

<210> SEQ ID NO 68
<211> LENGTH: 484
<212> TYPE: DNA
<213> ORGANISM: Propionibacterium acnes

<400> SEQUENCE: 68
gttgcacacc aggggtcaa cttggtgtcc tcagttcaaa attggttcaa actaacggtt        60
ccgtgtcggg aaacagcacc agaaaactcg tgacatatcg tctttcattg cgagaaacat       120
cttacttata cacatttcta agctatactg tctacccctg tcagacccag gacgatgggt       180
gtcatatccc ctttccagtc aacctaagaa gggaggaaat gccgcgatat atgttccgcc       240
ctgtcatcat gaatgccacc acaatctatc ccggaacagc cgtacttcac ccaccatgcc       300
ccgatgctgg attcctattg tcgcccttat tagagcaagc ggtgccagca gcagaatatt       360
tcacctcagc aactcgatcc gctcctgccc attacatggg taacatatcc atggaggtac       420
gatgtatgca tcgaggatgc agtcgtctac tatgcccgcc tacatacccc ttccatcagc       480
atag                                                                    484

<210> SEQ ID NO 69
<211> LENGTH: 484
<212> TYPE: DNA
<213> ORGANISM: Propionibacterium acnes

<400> SEQUENCE: 69
gttgcacacc aggggtcaa cttggtgtcc tcagttcaaa attggttcaa actaacggtt        60
ccgtgtcggg aaacagcacc agaaaacttg tgacatatcg tctttcattg cgagaaacat       120
cttacttata cacatttcta agctatattg tctacccctg tcagacccag gacgatgggt       180
gtcatatccc ctttccagtc aacctaagaa gggaggaaat gccgcgatat atgttccgcc       240
ctgtcatcat gaatgccacc acaatctatc ccggaacagc cgtacttcac ccaccatgcc       300
ccgatgctgg attcctattg tcgcccttat tagagcaagc ggtgccagca gcagaatatt       360
tcacctcagc aactcgatcc gctcctgccc attacatggg taacatatcc atggaggtac       420
```

-continued

```
gatgtatgca tcgaggatgc agtcgtctac tatgcccgcc tacataccca ttccatcagc      480
atag                                                                    484

<210> SEQ ID NO 70
<211> LENGTH: 484
<212> TYPE: DNA
<213> ORGANISM: Propionibacterium acnes

<400> SEQUENCE: 70
gttgcacacc aggggggtcaa cttggtgtcc tcagttcaaa attggttcaa actaacggtt       60
ccgtgtcggg aaacagcacc agaaaactca tgacatatcg tctttcattg cgagaaacat      120
cttacttata cacatttcta agctatattg tctacccctg tcagacccag gacgatgggt      180
gtcatatccc ctttccagtc aacctaagaa gggaggaaat gccgcgatat atgttccgcc      240
ctgtcatcat gaatgccacc acaatctatc ccggaacagc cgtacttcac ccaccatgcc      300
ccgatgctgg attcctattg tcgcccttat tagagcaagc ggtgccagca gcagaatatt      360
tcacctcagc aactcgatcc gctcctgccc attacatggg taacatatcc atggaggtac      420
gatgtatgca tcgaggatgc agtcgtctac tatgcccgcc tacataccca ttccatcagc      480
atag                                                                    484

<210> SEQ ID NO 71
<211> LENGTH: 484
<212> TYPE: DNA
<213> ORGANISM: Propionibacterium acnes

<400> SEQUENCE: 71
gttgcacacc aggggggtcaa cttggtgtcc tcagttcaaa attgattcaa actaacggtt       60
ccgtatcggg aaacagcacc agaaaactcg ggacatatcg tctttcattg cgagaaaaat      120
cttacttatg cgcatttcta agctatagcg tctacccttg tcagacccag gacgatgagt      180
gtcacatccc ctttccagtc aacctaagag aggaggaaat gccgcgatat atgctccgcc      240
ctgtcatcac gaaagccacc acaatctatc ccagaacagc cggcacttca ctcacgatgc      300
cccgatgctg gattcctatt gtcgccctta ttagggcaag cggtgccagt agcagaatat      360
gtcacctcag caactcgatc cgcccctgcc cattacatgg gtaacatatc catggaggtt      420
cgatgtatac tcgaggatac agtcgcccat cacgccagcc tacataccca ttacatcagc      480
atag                                                                    484

<210> SEQ ID NO 72
<211> LENGTH: 484
<212> TYPE: DNA
<213> ORGANISM: Propionibacterium acnes

<400> SEQUENCE: 72
gttgcacacc aggggggtcaa cttggtgtcc tcagttcaaa attgattcaa actaacggtt       60
ccgtatcggg aaacagcacc agaaaactcg ggacatatcg tctttcattg cgagaaaaat      120
cttacttatg cgcatttcta agctatagcg tctacccttg ccagacccag gacgatgagt      180
gtcacatccc ctttccagtc aacctaagag aggaggaaat gccgcgatat atgctccgcc      240
ctgtcatcac gaaagccacc acaatctatc ccagaacagc cggcacttca ctcacgatgc      300
cccgatgctg gattcctatt gtcgccctta ttagggcaag cggtgccagt agcagaatat      360
gtcacctcag caactcgatc cgcccctgcc cattacatgg gtaacatatc catggaggtt      420
cgatgtatac tcgaggatac agtcgcccat cacgccagcc tacataccca ttacatcagc      480
```

-continued atag                                                                    484

<210> SEQ ID NO 73
<211> LENGTH: 484
<212> TYPE: DNA
<213> ORGANISM: Propionibacterium acnes

<400> SEQUENCE: 73
gttgcacacc aggggtcaa cttggtgtcc tcagttcaaa attgattcaa actaacggtt      60
ccgtatcggg aaacagcacc agaaaactcg ggacatatcg tctttcattg cgagaaaaat     120
cttacttatg cgcatttcta agctatatcg tctacccttg ccagacccag gacgatgagt     180
gtcacatccc ctttccagtc aacctaagag aggaggaaat gccgcgatat atgctccgcc     240
ctgtcatcac gaaagccacc acaatctatc ccagaacagc cggcacttca ctcacgatgc     300
cccgatgctg gattcctatt gtcgccctta ttagggcaag cggtgccagt agcagaatat     360
gtcacctcag caactcgatc cgccctgcc cattacatgg gtaacatatc catggaggtt      420
cgatgtatac tcgaggatac agtcgcccat cacgccagcc tacatacccca ttacatcagc    480 atag                                                                    484

<210> SEQ ID NO 74
<211> LENGTH: 484
<212> TYPE: DNA
<213> ORGANISM: Propionibacterium acnes

<400> SEQUENCE: 74
gttgcacacc aggggtcaa cttggtgtcc tcagttcaaa attgattcaa actaacggtt      60
ccgtgtcggg aaacagcacc agaaaactcg ggacatatcg tctttcattg cgagaaaaat     120
cttacttatg cgcatttcta agctatagcg tctacccttg tcagacccag gacgatgagt     180
gtcacatccc ctttccagtc aacctaagag aggaggaaat gccgcgatat atgctccgcc     240
ctgtcatcac gaaagccacc acaatctatc ccagaacagc cggcacttca ctcacgatgc     300
cccgatgctg gattcctatt gtcgccctta ttagggcaag cggtgccagt agcagaatat     360
gtcacctcag caactcgatc cgccctgcc cattacatgg ttaacatatc catggaggtt      420
cgatgtatac tcgaggatac agtcgcccat cacgccagcc tacatacccca ttacatcagc    480 atag                                                                    484

<210> SEQ ID NO 75
<211> LENGTH: 484
<212> TYPE: DNA
<213> ORGANISM: Propionibacterium acnes

<400> SEQUENCE: 75
gttgcacacc aggggtcaa cttggtgtcc tcagttcaaa attgattcaa actaacggtt      60
ccgtgtcggg aaacagcacc agaaaactcg ggacatatcg tctttcattg cgagaaaaat     120
cttacttatg cgcatttcta agctatagcg tctacccttg tcagacccag gacgatgagt     180
gtcacatccc ctttccagtc aacctaagag aggaggaaat gccgcgatat atgctccgcc     240
ctgtcatcac gaaagccacc acaatctatc ccagaacagc cggcacttca ctcacgatgc     300
cccgatgctg gattcctatt gtcgccctta ttagggcaag cggtgccagt agcagaatat     360
gtcacctcag caactcgatc cgccctgcc cattacatgg ttaacatatc catggaggtt      420
cgatgtatac tcgaggatac agtcgcccat cacgccagcc tacatacccca ttacatcagc    480

-continued

```
atag                                                                484

<210> SEQ ID NO 76
<211> LENGTH: 484
<212> TYPE: DNA
<213> ORGANISM: Propionibacterium acnes

<400> SEQUENCE: 76
gttgcacacc aggggatcaa cttggtgtcc tcagttcaaa attgattcaa actaacggtt      60
ccgtatcggg aaacagcacc agaaaactcg ggacatatcg tctttcattg cgagaaaaat     120
cttacttatg cgcatttcta agctatagcg tctacccttg tcagacccag gacgatgagt     180
gtcacatccc ctttccagtc aacctaagag aggaggaaat gccgcgatat atgctccgcc     240
ctgtcatcac gaaagccacc acaatctatc ccagaacagc cggcacttca ctcacgatgc     300
cccgatgctg gattcctatt gtcgcccttta ttagggcaag cggtgccagt agcagaatat     360
gtcacctcag caactcgatc cgcccccgcc cattacatgg gtaacatatc catggaggtt     420
cgatgtatac tcgaggatac agtcgcccat cacgccagcc tacatacccca ttacatcagc     480 atag                                                                484

<210> SEQ ID NO 77
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 77
cagcggcgct gctaagaact t                                              21

<210> SEQ ID NO 78
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 78
ccggctggca aatgaggcat                                                20

<210> SEQ ID NO 79
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 79
tcgtcggcag cgtcagatgt gtataagaga cagcagcggc gctgctaaga actt           54

<210> SEQ ID NO 80
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 80
gtctcgtggg ctcggagatg tgtataagag acagccggct ggcaaatgag gcat           54

<210> SEQ ID NO 81
<211> LENGTH: 54
```

-continued

```
<212> TYPE: DNA
<213> ORGANISM: Artificial Sequence
<220> FEATURE:
<223> OTHER INFORMATION: Synthetic Polynucleotide

<400> SEQUENCE: 81
tcgtcggcag cgtcagatgt gtataagaga cagcagcggc gctgctaaga actt          54

<210> SEQ ID NO 82
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 82
gtctcgtggg ctcggagatg tgtataagag acagccggct ggcaaatgag gcat          54
```

SKIN CARE COMPOSITION

The present invention generally relates to the field of skin care. More particularly, the invention relates to a cosmetic or therapeutic skin care composition comprising live bacteria of at least one *Cutibacterium acnes* (*C. acnes*) strain in combination with a solubilizer that specifically supports their viability during storage and/or their ability to replicate after application to the skin. Preferably, the cosmetic or therapeutic skin care composition comprises bacteria of at least one *C. acnes* strain selected from the group consisting of D1, A5, C1, C3, H1, H2, H3, K1, K2, K4, K6, K8, K9, L1, and F4. The invention also provides a method for treating or preventing acne by applying the skin care composition of the invention to a skin area in need of treatment. The invention also relates to the use of a skin care composition of the invention for treating or preventing acne.

BACKGROUND OF THE INVENTION

Common acne is a widespread long-term skin condition that affects more than 600 million people worldwide. Acne is most common among teenagers, though it affects people of all ages. It is normally caused by a combination of sebaceous gland hyperplasia, excessive sebum production, and impaired cornification. As a result, the hair follicles become plugged with oil and dead skin cells which leads to pimples and oily skin (Pschyrembel, Klinisches Wörterbuch, 258. ed., Walter de Gruyter-Verlag, Berlin, 1998). The colonization of the affected skin area with bacteria may additionally cause inflammation. Acne predominantly affects skin areas with a high number of sebaceous glands, in particular the face, the upper part of the chest, and the back. The occurrence of acne may lead to emotional distress and mental problems, such as reduced self-esteem and depression.

Oily skin is a transition state between healthy skin and acne-prone skin. In oily skin, the sebaceous glands of the skin produce an excessive amount of sebum which then serves as an ideal nutrient for a number bacteria and yeasts, including the anaerobic gram-positive bacterium *Cutibacterium acnes* (formerly known as *Propionibacterium acnes*) and different species of the yeast genus *Pityrosporum*. These microorganisms decompose the sebum to glycerine and fatty acids, thereby further inducing the production of sebum in the sebaceous glands and destroying the follicle walls in the skin. This results in inflammation of the skin and the formation of pimples, pustules, nodules and cysts which often heal only with scarring which permanently affects the optical appearance of the subject's skin (W. Umbach [Ed.], Kosmetik, Entwicklung, Herstellung and Anwendung kosmetischer Mittel, 2. Edition Thieme Verlag, Stuttgart, 1995).

A number of different factors appear to contribute to the occurrence of acne, including genetics, hormone status, stress and diet. In addition, the anaerobic bacterial species *Cutibacterium acnes* (formerly *Propionibacterium acnes*) is thought to play an important role in the development of acne, since high numbers of these bacteria are regularly found in patients suffering from moderate or severe inflammatory acne. However, the underlying mechanisms are not completely understood.

Today, the standard treatment for acne normally includes the topical application of antibiotics, including erythromycin, clindamycin, metronidazole, sulfacetamide, doxycycline or minocycline, to reduce the number of bacteria, especially *C. acnes*. However, some of these antibiotics exhibit considerable side effects which make their use inconvenient for the patient. In addition, the treatment of acne with antibiotics is associated with high relapse rates due to the fact that small populations of *C. acnes* survive and resume growth after termination of the antibiotic treatment. Accordingly, there is a need for new methods of treating or preventing acne which is essentially free of side effects and provides for a long-lasting effect.

In more recent treatment approaches, acne has been considered to be the result of a distortion of the human skin microbiome caused by specific strains of *C. acnes* (Holmes, 2013; Lomholt and Kilian, 2010). Researchers only recently began to investigate the skin microbiome (Belkaid and Segre, 2014; Oh et al., 2014). While the skin is colonized by a large number of microorganisms which are harmless or even beneficial (Grice and Segre, 2011), alterations of the microbiome can result in diseases such as acne (Bek-Thomsen et al., 2008; Holmes, 2013; Kong et al., 2012, Fitz-Gibbon et al., 2013). This distortion is likely caused by a specific subset of the skin bacterium *C. acnes* (Lomholt and Kilian, 2010). It has therefore been suggested to modulate the skin microbiome in the attempt to restore a healthy microbiome. For example, WO 2016/172196 A1 discloses a method of treating acne in a subject by first administering a disinfectant or antibiotic and subsequently administering a composition comprising one or more live *C. acnes* strain to the skin of the subject. Similarly, WO 2018/073651 A1 discloses a composition for acne treatment comprising two or more different *C. acnes* strains, including *C. acnes* strain C3 and/or K8.

SUMMARY OF THE INVENTION

In a first aspect, the invention relates to a skin care composition for topical administration to the skin comprising (a) lyophilized or spray-dried live bacteria of at least one *Cutibacterium acnes* (*C. acnes*) strain; and (b) PEG-40 hydrogenated castor oil as a solubilizer.

In some embodiments, PEG-40 hydrogenated castor oil is present in the skin care composition in an amount of 0.01 to 2.5% (w/w). In some embodiments, PEG-40 hydrogenated castor oil is present in the skin care composition in an amount of 0.05 to 1.5% (w/w). In some embodiments, PEG-40 hydrogenated castor oil is present in the skin care composition in an amount of 0.5 to 1.0% (w/w).

In some embodiments, the skin care composition does not comprise any other solubilizer except for PEG-40 hydrogenated castor oil.

In some embodiments, the skin care composition further comprises an emollient selected from the group consisting of dicaprylyl carbonate, ethylhexyl cocoate, and mixtures thereof.

In some embodiments, the skin care composition further comprises a filler selected from the group consisting of distarch phosphate, tapioca starch, and mixtures thereof.

In some embodiments, the skin care composition further comprises a thickener selected from the group consisting of a *Chondrus crispus* extract, hydroxypropyl starch phosphate, and mixtures thereof.

In some embodiments, the skin care composition further comprises a preservative selected from the group consisting of ethanol, phenoxyethanol, caprylyl glycol, methylpropanediol, and mixtures thereof.

In some embodiments, the skin care composition further comprises an antioxidant selected from the group consisting of tocopherol, tocopheryl acetate, and mixtures thereof.

In some embodiments, the skin care composition further comprises citric acid/citrate buffer as a pH adjuster.

In some embodiments, the skin care composition comprises at least one *C. acnes* strain selected from the group consisting of single locus sequence typing (SLST) type strains D1, A5, C1, C3, H1, H2, H3, K1, K2, K4, K6, K8, K9, L1, and F4. In some embodiments, the skin care composition comprises lyophilized or spray-dried live bacteria of at least one *C. acnes* SLST type C3 strain. In some embodiments, the skin care composition comprises lyophilized or spray-dried live bacteria of at least one *C. acnes* SLST type K8 strain. In some embodiments, the skin care composition comprises lyophilized or spray-dried live bacteria of at least one *C. acnes* SLST type C3 strain and at least one *C. acnes* SLST type K8 strain.

In some embodiments, the skin care composition further comprises lyophilized or spray-dried live bacteria of at least one *C. acnes* SLST type A5 strain. In some embodiments, the skin care composition further comprises lyophilized or spray-dried live bacteria of at least one *C. acnes* SLST type F4 strain.

In some embodiments, the concentration of each *C. acnes* strain is at least 0.5% (w/v) of the skin care composition. In some embodiments, the at least one *C. acnes* SLST type C3 strain and at least one *C. acnes* SLST type K8 strain are at approximately equal concentrations within the composition. In some embodiments, the at least one *C. acnes* SLST type C3 strain is present at a higher concentration than said at least one *C. acnes* SLST type K8 strain within the composition. In other embodiments, the at least one *C. acnes* SLST type K8 strain is present at a higher concentration than said at least one *C. acnes* SLST type C3 strain within the composition.

In some embodiments, each of the *C. acnes* strains in the composition is present in an amount of $10^4$-$10^{11}$ colony forming units per ml (CFU/ml), preferably $10^7$-$10^{10}$ CFU/ml. In some embodiments, the overall amount of bacteria in the composition is $10^4$-$10^{11}$ CFU/ml, preferably $10^7$-$10^{10}$ CFU/ml.

In some embodiments, the skin care composition is in the form of a gel, cream, ointment or lotion.

In a second aspect, the invention relates to a method of improving the appearance of the skin of a subject and/or modulating the sebum production of skin cells of a subject and/or maintaining healthy skin of a subject, said method comprising the topical administration of a skin care composition of the invention. In some embodiments, the subject is a human.

In a third aspect, the invention relates to a method of treating or preventing a condition selected from the group consisting of acne, oily skin, progressive macular hypomelanosis, dandruff, atopic eczema, atopic dermatitis and rosacea in a subject, said method comprising the topical administration of a skin care composition of the invention. In some embodiments, the subject is a human.

BRIEF DESCRIPTION OF THE FIGURE

FIG. 1 shows the composition of prototype formulations 1-15 used in the reactivation experiments with freeze-dried bacteria.

FIG. 4 shows the composition of additional prototype formulations 1-11 used in reactivation experiments with freeze-dried bacteria.

FIG. 5 shows the results from experiments analyzing the reactivation of freeze-dried bacteria from the additional prototype formulations 1-11.

FIG. 6 shows the results from experiments analyzing the reactivation of freeze-dried bacteria from comparative formulations V1-V10.

FIG. 7 shows the composition of comparative formulations V1-V10 used in reactivation experiments with freeze-dried bacteria.

DETAILED DESCRIPTION

Figure 2:
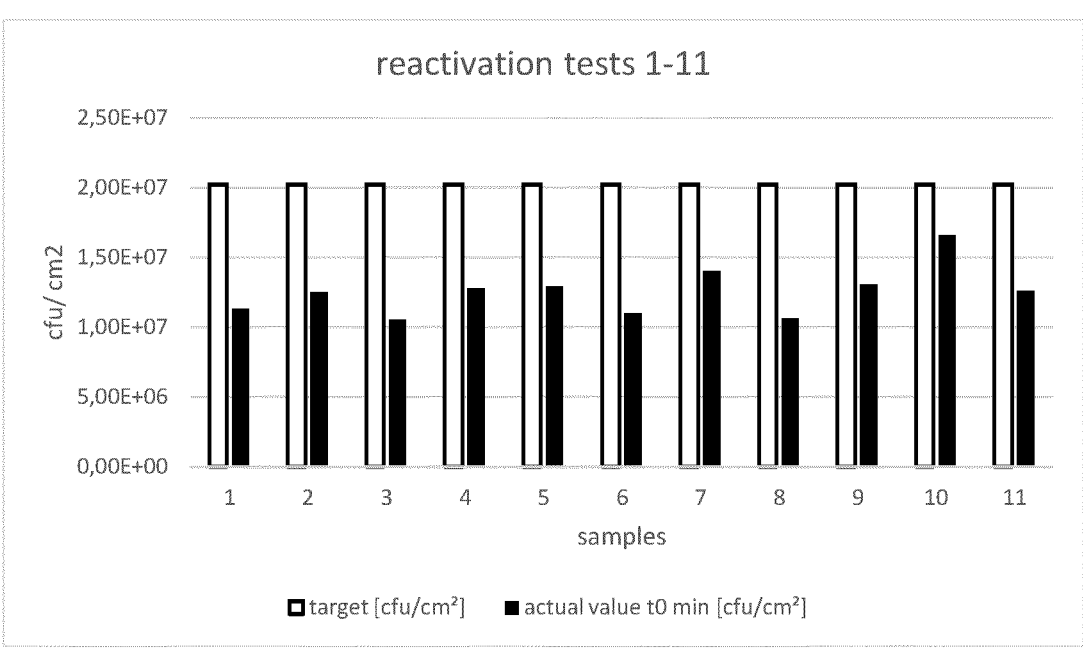
FIG. 2 shows the results from experiments analyzing the reactivation of freeze-dried bacteria from prototype formulations 1-11.

While these method and compositions provide for a novel and highly effective modulation of the microbiome which ameliorates or eliminates the symptoms of acne, the provision of live bacteria in cosmetic skin care compositions has been found to be associated with significant problems. For example, some of the components commonly used in commercial skin care products interfere with bacterial viability. When these compounds are combined into compositions with lyophilized or spray-dried bacteria, they can either interfere with the viability of the bacteria or negatively influence their growth rate after application to the skin. Accordingly, there is a need for novel skin care products which have been formulated in a way to be compatible with the application of lyophilized or spray-dried bacteria and which do not inhibit the outgrowth of these bacteria after application of the product to a skin.

It has now been surprisingly found that the viability of lyophilized or spray-dried bacteria, in particular bacterial strains of the species *C. acnes*, during storage in the skin care composition as well as their ability to grow upon application to skin can be preserved or significantly improved by the excipients which are added to the formulation of the final skin care product. The present invention is based on the identification of a group of excipients for use in skin care compositions which do not significantly interfere with or may improve bacterial viability and reactivation of growth. These compounds have been found to be highly compatible the administration of bacteria, in particular bacterial strains of the species *C. acnes*.

Thus, in a first aspect the present invention relates to a skin care composition for topical administration to the skin, said composition comprising, consisting essentially of, or consisting of (a) lyophilized or spray-dried live bacteria of at least one *C. acnes* strain; and (b) PEG-40 hydrogenated castor oil as a solubilizer.

In the context with the present invention, lyophilized or spray-dried live bacteria are used in the skin care composition. This means that viable bacteria have been subjected to a drying process that maintains their viability, but reduces their metabolic processes to minimum. In lyophilized or spray-dried form, the bacteria can be stored for months or even years. Once they are applied to the skin, such as the human skin, the metabolism of the bacteria is reactivated such that they resume growth. They propagate on the skin surface and displace pathogenic bacterial strains, thereby recovering a diverse, healthy and balanced skin microbiome.

In one embodiment, the live *C. acnes* bacteria are present in spray-dried form. The principle of spray drying is based on the dispersion of a solution into fine droplets which are introduced into a flow of hot air. The solvent evaporates from the substrate droplets so that dry product clusters remain. Standard spray drying devices can be used, such as the Mini Spray Dryer B-290 from Büchi Labortechnik GmbH (Essen, Germany) or the Mobile Minor™ Spray Dryer from GEA (Berlin, Germany).

In one embodiment, the live *C. acnes* bacteria are present in freeze-dried or lyophilized form. Freeze drying or lyophilization is a process which includes freezing the product, reducing the pressure and adding heat to allow the frozen water in the material to sublimate. Various methods can be applied for freezing the product. For example, freezing can be achieved by using a standard freezer or a chilled bath. Cooling the product below its triple point ensures that sublimation will occur upon heating. To prevent the formation of large crystals that may damage the structure of the product to be dried, freezing is done rapidly. About 95% of the water in the product is removed when the frozen water sublimates. Most materials can be dried to 1-5% residual moisture. Standard freeze drying devices can be used, such as the Lyovac™ devices from GEA (Berlin, Germany), the Gamma 2-20 Freeze dryer LCM-1 from Christ (Osterode am Harz, Germany), or the Christ Martin™ Alpha 1-2 Lyophilisator from Fisher Scientific GmbH (Schwerte, Germany).

The one or more excipients that do not interfere with viability and reactivation of growth of said lyophilized or spray-dried live bacteria are selected from the group consisting of emollients, thickeners, fillers, antioxidants, preservatives, solubilizers, and pH adjusters. Suitable members for each of these groups of compounds will be discussed herein below.

Solubilizer

According to the present invention, the skin care composition comprises a solubilizer. As used herein, a solubilizer is a compound that aids in the solubilization of hydrophobic substances in aqueous and alcoholic formulations. For example, a solubilizer may render feasible the solubilization of perfume oils and other hydrophobic substances, such as vitamins, into an aqueous skin care composition. It has been found herein that polyethylene glycol (PEG)-40 hydrogenated castor oil does not interfere with viability and replication capability of the lyophilized or spray-dried bacteria.

According to the present invention, the skin care composition comprising the lyophilized or spray-dried live bacteria of at least one *C. acnes* strain comprises PEG-40 hydrogenated castor oil as a solubilizer. In an even more preferred embodiment, PEG-40 hydrogenated castor oil is the only solubilizer included in the composition.

When PEG-40 hydrogenated castor oil is used as solubilizer, it is preferably used in the final skin care composition in an amount of 0.01 to 2.5% (w/w), more preferably 0.05 to 1.5% (w/w), and more preferably 0.5 to 1.0% (w/w). Stated differently, the amount of PEG-40 hydrogenated castor oil in the skin care composition of the invention may be at least 0.01% (w/w), at least 0.05% (w/w), at least 0.1% (w/w), at least 0.2% (w/w), at least 0.3% (w/w), at least 0.4% (w/w), at least 0.5% (w/w), at least 0.6% (w/w), at least 0.7% (w/w), at least 0.8% (w/w), at least 0.9% (w/w), or at least 1.0% (w/w).

Emollient

In a preferred aspect, the skin care composition further comprises an emollient. As used herein, an emollient is a compound that moisturizes and/or softens the skin. Emollients normally reduce the roughness, cracking and/or irritation of the skin by penetrating into the deeper layers of the skin. Emollients commonly used in skin care products comprise plant oils, like sesame oil, coconut oil, olive oil, almond oil, macadamia nut oil, cottonseed oil or peanut oil, silicone oils, like dimethylpolysiloxane and cyclomethicone, fatty acids, and fatty alcohol ethers.

In a preferred embodiment, the skin care composition comprising the lyophilized or spray-dried live bacteria of at least one *C. acnes* strain and the above-defined solubilizer comprises an emollient selected from the group consisting of dicaprylyl carbonate, ethylhexyl cocoate, and mixtures thereof. In one preferred embodiment, the skin care composition comprises lyophilized or spray-dried live bacteria of at least one *C. acnes* strain, the solubilizer and dicaprylyl carbonate as an emollient. In another preferred embodiment, the skin care composition comprises lyophilized or spray-dried live bacteria of at least one *C. acnes* strain, the solubilizer and ethylhexyl cocoate as an emollient. In yet another preferred embodiment, the skin care composition comprises lyophilized or spray-dried live bacteria of at least one *C. acnes* strain, the solubilizer and both dicaprylyl carbonate and ethylhexyl cocoate as emollients. It is particularly preferred that the skin care composition does not comprise any other emollient except for dicaprylyl carbonate and/or ethylhexyl cocoate.

When dicaprylyl carbonate is used as an emollient, it is preferably used in the final skin care composition in an amount of 0.05 to 25.0% (w/w), more preferably 2.0 to 20.0% (w/w), and more preferably 5.0 to 10.0% (w/w) or 7.5 to 10.0% (w/w). Stated differently, the amount of dicaprylyl carbonate in the skin care composition of the invention may be at least 0.05% (w/w), at least 0.1% (w/w), at least 0.25% (w/w), at least 0.5% (w/w), at least 0.75% (w/w), at least 1.0% (w/w), at least 1.25% (w/w), at least 1.5% (w/w), at least 1.75% (w/w), at least 2.0% (w/w), at least 2.5% (w/w), at least 3.0% (w/w), at least 4.0% (w/w), at least 5.0% (w/w), at least 6.0% (w/w), at least 7.0% (w/w), at least 8.0% (w/w), or at least 9.0% (w/w).

When ethylhexyl cocoate is used as an emollient, it is preferably used in the final skin care composition in an amount of 0.05 to 25.0% (w/w), more preferably 1.0 to 10.0% (w/w), and more preferably 5.0 to 10.0% (w/w), or 7.5 to 10.0% (w/w). Stated differently, the amount of ethylhexyl cocoate in the skin care composition of the invention may be at least 0.05% (w/w), at least 0.1% (w/w), at least 0.25% (w/w), at least 0.5% (w/w), at least 0.75% (w/w), at least 1.0% (w/w), at least 1.25% (w/w), at least 1.5% (w/w), at least 1.75% (w/w), at least 2.0% (w/w), at least 2.5% (w/w), at least 3.0% (w/w), at least 4.0% (w/w), at least 5.0% (w/w), at least 6.0% (w/w), at least 7.0% (w/w), at least 8.0% (w/w), or at least 9.0% (w/w).

When dicaprylyl carbonate and ethylhexyl cocoate are used in combination with each other as emollients, it is preferred that the overall amount of emollient is at least 0.05% (w/w), but does not exceed 20.0% (w/w), more preferably does not exceed 15.0% (w/w) or 10.0% (w/w). In such an embodiment, it is furthermore preferred that dicaprylyl carbonate and ethylhexyl cocoate are used in equal amounts, for example, 2.0% (w/w) dicaprylyl carbonate in combination with 2.0% (w/w) ethylhexyl cocoate, or 5.0% (w/w) dicaprylyl carbonate in combination with 5.0% (w/w) ethylhexyl cocoate.

Thickener

In another preferred aspect, the skin care composition further comprises a thickener. Thickeners are compounds that increase the viscosity of a cosmetic or pharmaceutical formulation. Thickeners are often polymers that absorb water and swell up, thereby making the composition more viscous. Thickeners commonly used in skin care products comprise bean gum, xanthan gum, gelatin, Carnauba wax, and stearic acid.

According to the present invention, the skin care composition comprising the lyophilized or spray-dried live bacteria of at least one *C. acnes* strain and the above-defined solubilizer comprises a thickener selected from the group consisting of a *C. crispus* extract, hydroxypropyl starch phosphate, and mixtures thereof. In one preferred embodiment, the skin care composition comprises lyophilized or spray-dried live bacteria of at least one *C. acnes* strain, the solubilizer and a *C. crispus* extract as a thickener. In another preferred embodiment, the skin care composition comprises lyophilized or spray-dried live bacteria of at least one *C. acnes* strain, the solubilizer and hydroxypropyl starch phosphate as a thickener.

When a *C. crispus* extract is used as a thickener, it is preferably used in the final skin care composition in an amount of 0.05 to 7.5% (w/w), more preferably 0.1 to 5.0% (w/w), and even more preferably 0.2 to 4.0% (w/w), 0.2 to 2.0% (w/w), or 0.2 to 1.5% (w/w). Stated differently, the amount of the *C. crispus* extract in the skin care composition of the invention may be at least 0.05% (w/w), at least 0.1% (w/w), at least 0.25% (w/w), at least 0.5% (w/w), at least 0.75% (w/w), at least 1.0% (w/w), at least 1.25% (w/w), at least 1.5% (w/w), at least 1.75% (w/w), at least 2.0% (w/w), at least 2.5% (w/w), at least 3.0% (w/w), at least 4.0% (w/w), or at least 5.0% (w/w).

When hydroxypropyl starch phosphate is used as a thickener, it is preferably used in the final skin care composition in an amount of 0.05 to 10.0% (w/w), more preferably 0.1 to 10.0% (w/w), and even more preferably 0.5 to 7.5% (w/w), 1.0 to 5.0% (w/w), or 1.0 to 2.0% (w/w). Stated differently, the amount of hydroxypropyl starch phosphate in the skin care composition of the invention may be at least 0.05% (w/w), at least 0.1% (w/w), at least 0.25% (w/w), at least 0.5% (w/w), at least 0.75% (w/w), at least 1.0% (w/w), at least 1.25% (w/w), at least 1.5% (w/w), or at least 1.75% (w/w).

It should be understood that the skin care composition of the present invention may also comprise a combination of a *C. crispus* extract and hydroxypropyl starch phosphate as thickeners. When the *C. crispus* extract and hydroxypropyl starch phosphate are used in combination with each other as thickeners, it is preferred that the overall amount of thickeners is at least 0.05% (w/w), but does not exceed 10.0% (w/w), more preferably does not exceed 5.0% (w/w). In such an embodiment, it is furthermore preferred that two thickeners are used in equal amounts, for example, 2.0% (w/w) *C. crispus* extract and 2.0% (w/w) hydroxypropyl starch phosphate.

pH Adjuster

In another preferred aspect, the skin care composition of the present invention further comprises a pH adjuster. Since the composition of the invention is used on the human skin, it will preferably have a neutral or slightly acidic pH to make it more compatible with the acidic environment of the skin. The composition may have a pH in the range from about 2.5 to about 7.5, preferably from about 4.0 to about 7.0, and more preferably from about 6.0 to about 7.0. While an acidic pH in a cosmetic formulation is normally achieved by adding an acid, such as formic acid, acetic acid, butyric acid, valeric acid, caproic acid, enanthic acid, or caprylic acid, it has been found that these acids could compromise the ability of the bacteria in the composition to grow and replicate after administration to the skin. According to the invention, the pH adjuster preferably is a citric acid/citrate buffer.

Therefore, in another preferred aspect, the skin care composition comprising the lyophilized or spray-dried live bacteria of at least one *C. acnes* strain and the solubilizer also comprises a citric acid/citrate buffer, such as for example a citric acid/sodium citrate buffer, as a pH adjuster. In a preferred embodiment, the skin care composition comprises lyophilized or spray-dried live bacteria of at least one *C. acnes* strain, the solubilizer and a buffer consisting of citric acid and sodium citrate. It is particularly preferred that the skin care composition does not comprise any other pH adjuster except for citric acid/citrate.

When citric acid is used as a pH adjuster, it is preferably used in the final skin care composition in an amount of 0.01 to 1.5% (w/w), more preferably 0.01 to 0.25% (w/w), and even more preferably 0.01 to 0.1% (w/w). Stated differently, the amount of citric acid in the skin care composition of the invention may be at least 0.01% (w/w), at least 0.02% (w/w), at least 0.03% (w/w), at least 0.04% (w/w), at least 0.05% (w/w), at least 0.06% (w/w), at least 0.07% (w/w), at least 0.08% (w/w), at least 0.09% (w/w), or at least 0.1% (w/w).

When sodium citrate is used as a pH adjuster, it is preferably used in the final skin care composition in an amount of 0.01 to 1.5% (w/w), more preferably 0.05 to 1.0% (w/w), and more preferably 0.05 to 0.5% (w/w) or 0.1 to 0.2% (w/w). Stated differently, the amount of sodium citrate in the skin care composition of the invention may be at least 0.01% (w/w), at least 0.02% (w/w), at least 0.03% (w/w), at least 0.04% (w/w), at least 0.05% (w/w), at least 0.06% (w/w), at least 0.07% (w/w), at least 0.08% (w/w), at least 0.09% (w/w), at least 0.1% (w/w), 0.11% (w/w), 0.12% (w/w), 0.13% (w/w), 0.14% (w/w), 0.15% (w/w), 0.16% (w/w), 0.17% (w/w), 0.18% (w/w), 0.19% (w/w), 0.2% (w/w), at least 0.3% (w/w), at least 0.4% (w/w), at least 0.5% (w/w), at least 0.6% (w/w), at least 0.7% (w/w), at least 0.8% (w/w), at least 0.9% (w/w), or at least 1.0%.

When citric acid and sodium citrate are used in combination with each other as pH adjusters, it is preferred that the overall amount of the pH adjusters in the final skin care composition does not exceed 0.3% (w/w). In such an embodiment, it is furthermore preferred that citric acid and sodium citrate are used in a ratio of 1:2, for example, 0.05% (w/w) citric acid and 0.10% (w/w) sodium citrate, or 0.1% (w/w) citric acid in combination with 0.2% (w/w) sodium citrate.

It is particularly preferred that citric acid and the citrate are used in the skin care composition of the invention in amounts which ensure a pH of between 5.0 and 7.0 of the overall composition.

Filler

In yet another preferred aspect, the skin care composition further comprises a filler. As used herein, a filler is a compound that aids in making the skin care composition more homogeneous by uniformly dispersing in the composition. Fillers are used to improve the sensory properties of the skin. Depending on the filler material, the end product may confer a silky, dry, smooth, or powdery skin feel.

According to another preferred aspect of the present invention, the skin care composition comprising the lyophilized or spray-dried live bacteria of at least one *C. acnes* strain and the above-defined solubilizer comprises a filler selected from the group consisting of distarch phosphate, tapioca starch, and mixtures thereof. In one preferred embodiment, the skin care composition comprises lyophilized or spray-dried live bacteria of at least one *C. acnes* strain, the solubilizer and distarch phosphate as a filler. In another preferred embodiment, the skin care composition comprises lyophilized or spray-dried live bacteria of at least one *C. acnes* strain, the solubilizer and tapioca starch as a filler. In yet another preferred embodiment, the skin care composition comprises lyophilized or spray-dried live bacteria of at least one *C. acnes* strain, the solubilizer and both distarch phosphate and tapioca starch as fillers. It is preferred that the skin care composition does not comprise any other filler except for distarch phosphate and/or tapioca starch.

When distarch phosphate is used as filler, it is preferably used in the final skin care composition in an amount of 0.05 to 5.0% (w/w), more preferably 1.0 to 5.0% (w/w), and more preferably 2.0 to 5.0% (w/w) or 2.0 to 3.0% (w/w). Stated differently, the amount of distarch phosphate in the skin care composition of the invention may be at least 0.05% (w/w), at least 0.1% (w/w), at least 0.25% (w/w), at least 0.5% (w/w), at least 0.75% (w/w), at least 1.0% (w/w), at least 1.25% (w/w), at least 1.5% (w/w), at least 1.75% (w/w), at least 2.0% (w/w), at least 2.5% (w/w), at least 3.0% (w/w), or at least 4.0% (w/w). The same amounts apply when using tapioca starch as filler.

When distarch phosphate and tapioca starch are used in combination with each other as fillers, it is preferred that the overall amount of the fillers is at least 0.05% (w/w), but does not exceed 5.0% (w/w), more preferably does not exceed 3.0% (w/w). In such an embodiment, it is furthermore preferred that distarch phosphate and tapioca starch are used in equal amounts, for example, 2.5% (w/w) distarch phosphate in combination with 2.5% (w/w) tapioca starch, or 1.0% (w/w) distarch phosphate in combination with 1.0% (w/w) tapioca starch.

Antioxidant

In another preferred aspect, the skin care composition further comprises an antioxidant. These compounds are normally added to cosmetic formulations to prevent oxidative reactions catalyzed by oxygen radicals that would otherwise result in the decomposition of ingredients in the composition, such as proteins, sugars, and lipids. Antioxidants which are commonly used in cosmetic product include chemicals like butylated hydroxytoluene and butylated hydroxyanisole, as well as plant derived polyphenols, flavonoids, flavanols, stilbens, and terpenes.

In a preferred embodiment, the skin care composition comprises the lyophilized or spray-dried live bacteria of at least one *C. acnes* strain, the above-defined solubilizer and an antioxidant selected from the group consisting of tocopherol, tocopheryl acetate, and mixtures thereof. In one preferred embodiment, the skin care composition comprises lyophilized or spray-dried live bacteria of at least one *C. acnes* strain, the solubilizer and tocopherol as an antioxidant. In another preferred embodiment, the skin care composition comprises lyophilized or spray-dried live bacteria of at least one *C. acnes* strain, the solubilizer and tocopheryl acetate as an antioxidant. In yet another preferred embodiment, the skin care composition comprises lyophilized or spray-dried live bacteria of at least one *C. acnes* strain, the solubilizer and both tocopherol and tocopheryl acetate as antioxidants. It is particularly preferred that the skin care composition does not comprise any other antioxidant except for tocopherol and/or tocopheryl acetate.

When tocopherol, tocopheryl acetate, or mixtures thereof are used as antioxidants, they can be added in lyophilized or spray-dried form to the lyophilized or spray-dried live bacteria. For example, if the composition of the invention is provided in a form that requires the mixing of the bacteria with a cosmetic or pharmaceutical preparation prior to use, the lyophilized or spray-dried antioxidants may be added to the lyophilized or spray-dried bacteria and stored until reconstitution with the cosmetic or pharmaceutical preparation until use. Where tocopherol, tocopheryl acetate, or mixtures thereof are used in dried form, dried vitamin C may also be added.

When tocopherol is used as an antioxidant, it is preferably used in the final skin care composition in an amount of 0.01 to 2.0% (w/w), more preferably 0.05 to 1.5% (w/w), and more preferably 0.1 to 1.0% (w/w). Stated differently, the amount of tocopherol in the skin care composition of the invention may be at least 0.01% (w/w), at least 0.025% (w/w), at least 0.05% (w/w), at least 0.075% (w/w), at least 0.1% (w/w), at least 0.2% (w/w), at least 0.3% (w/w), at least 0.4% (w/w), at least 0.5% (w/w), at least 0.6% (w/w), at least 0.7% (w/w), at least 0.8% (w/w), at least 0.9% (w/w), or at least 1.0% (w/w). The same amounts apply when using tocopheryl acetate as antioxidant.

When tocopherol and tocopheryl acetate are used in combination with each other as antioxidants, it is preferred that the overall amount of antioxidants is at least 0.01% (w/w), but does not exceed 2.0% (w/w). In such an embodiment, it is furthermore preferred that tocopherol and tocopheryl acetate are used in equal amounts, for example, 0.25% (w/w) tocopherol in combination with 0.25% (w/w) tocopheryl acetate, or 0.5% (w/w) tocopherol in combination with 0.5% (w/w) tocopheryl acetate.

Preservatives

In another preferred aspect, the skin care composition further comprises a preservative. As used herein, a preservative is a compound that is added to cosmetic formulation to prevent microbial spoilage of the formulation by inhibiting the growth of unintended bacteria and yeasts. Commonly used preservatives for cosmetic formulations include, amongst others, benzyl alcohol, salicylic acid and sorbic acid.

In a preferred embodiment, the skin care composition comprises the lyophilized or spray-dried live bacteria of at least one *C. acnes* strain, the above-defined solubilizer and a preservative selected from the group consisting of ethanol, phenoxyethanol, caprylyl glycol, methylpropanediol, and mixtures thereof. These preservatives are surprisingly tolerated to some extent by *C. acnes* strains while being effective against other bacteria that may contaminate the composition.

In one preferred embodiment, the skin care composition comprises lyophilized or spray-dried live bacteria of at least one *C. acnes* strain, the solubilizer and ethanol as a preservative. In another preferred embodiment, the skin care composition comprises lyophilized or spray-dried live bacteria of at least one *C. acnes* strain, the solubilizer and phenoxyethanol as a preservative. In yet another preferred embodiment, the skin care composition comprises lyophilized or spray-dried live bacteria of at least one *C. acnes* strain, the solubilizer and caprylyl glycol as a preservative. In yet another preferred embodiment, the skin care composition comprises lyophilized or spray-dried live bacteria of at least one *C. acnes* strain, the solubilizer and methylpropanediol as a preservative.

The skin care composition of the present invention may furthermore comprise more than one preservative, e.g. two or more of the above mentioned preservatives. For example, the composition may comprise ethanol in combination with phenoxyethanol as preservatives. Alternatively, the composition may comprise ethanol in combination with caprylyl glycol as preservatives. Alternatively, the composition may comprise ethanol in combination with methylpropanediol as preservatives. The composition may also comprise phenoxyethanol in combination with caprylyl glycol as preservatives or a combination of phenoxyethanol in combination with methylpropanediol as preservatives. The composition may also comprise caprylyl glycol in combination with methyl-propanediol as preservatives.

The best results in terms of protecting the skin care composition of the invention from spoilage with other bacteria or fungi and, at the same time, maintain the viability of the lyophilized or spray-dried live C. acnes bacteria in the composition are obtained with a combination of phenoxy-ethanol, caprylyl glycol and methylpropanediol. Hence, in a particular preferred embodiment, the skin care composition of the present invention comprises lyophilized or spray-dried live bacteria of at least one C. acnes strain, an antioxidant and a combination of phenoxyethanol, caprylyl glycol and methylpropanediol.

When ethanol is used as a preservative, it is preferably used in the final skin care composition in an amount of 0.5 to 20.0% (w/w), more preferably 8.0 to 15.0% (w/w), and more preferably 5.0 to 15.0% (w/w). Stated differently, the amount of ethanol in the skin care composition of the invention may be at least 0.5% (w/w), at least 1.0% (w/w), at least 2.0% (w/w), at least 3.0% (w/w), at least 4.0% (w/w), at least 5.0% (w/w), at least 6.0% (w/w), at least 7.0% (w/w), at least 8.0% (w/w), at least 9.0% (w/w), or at least 10.0% (w/w).

When phenoxyethanol is used as a preservative, it is preferably used in the final skin care composition in an amount of 0.05 to 0.5% (w/w), more preferably 0.1 to 0.25% (w/w), and more preferably 0.1 to 0.2% (w/w). Stated differently, the amount of phenoxyethanol in the skin care composition of the invention may be at least 0.05% (w/w), at least 0.075% (w/w), at least 0.1% (w/w), at least 0.15% (w/w), at least 0.2% (w/w), or at least 0.25% (w/w). The same amounts apply when using caprylyl glycol as a pre-servative.

When methylpropanediol is used as a preservative, it is preferably used in the final skin care composition in an amount of 0.05 to 5.0% (w/w), more preferably 0.5 to 2.5% (w/w), and more preferably 1.0 to 1.5% (w/w). Stated differently, the amount of methylpropanediol ethanol in the skin care composition of the invention may be at least 0.5% (w/w), at least 1.0% (w/w), at least 2.0% (w/w), at least 3.0% (w/w), or at least 4.0% (w/w), or at least 5.0% (w/w).

When two or more of the above preservatives are used in combination with each other, it is preferred that the overall amount of preservative does not exceed 5.0% (w/w) when using a combination of phenoxyethanol and caprylyl glycol. In particular, when using caprylyl glycol, phenoxyethanol, and methylpropanediol in combination, it is preferred to use these compounds in a ratio of 1:2:20, for example, 0.05% (w/w) caprylyl glycol, 0.1% (w/w) phenoxyethanol, and 1.0% (w/w) methylpropanediol, or alternatively, 0.1% (w/w) caprylyl glycol, 0.2% (w/w) phenoxyethanol, and 2.0% (w/w) methylpropanediol.

The above-mentioned preservatives can be used in com-bination with other preservatives, in particular short-chain fatty acids such as formic acid, propionic acid or isobutyric acid. In addition, the compositions of the invention may also comprise lactic acid as an additional preservative.

Other Cosmetic Excipients

The skin care compositions described herein may include, apart from the above components, commonly known excipi-ents, including perfumes, pigments, colorants, dyes, waxes, masking agents, humectants, surfactants, lubricants, stabi-lizers, sunscreens, emulsifiers, medicaments, antiseptics, chelating agents, protectants, viscosifiers, vitamins, panthe-nol, ubiquinone Q10, hyaluronic acid, or any combinations thereof.

Bacterial Strains

The skin care composition of the present invention com-prises lyophilized or spray-dried live bacteria of at least one strain of the species C. acnes. It will however be preferred that the skin care composition comprises two or more strains of the species C. acnes. For example, the skin care compo-sition may comprise 2, 3, 4, 5, 6, 7, 8, 9, 10, 11, 12, 13, 14, 15, 16, 17, 18, 19, 20 or more than 20 strains of C. acnes. In some embodiments, the skin care composition comprises 2, 3, 4, or 5 different strains of C. acnes. It was reported that the reactivation and growth of some C. acnes strains is significantly supported when grown in a mixture of strains than when grown individually. For example, SLST type strain K8 grows slowly individually, but significantly faster when grown within a mixture of strains. Therefore, it is preferred according to the present invention that the com-position comprises two or more strains of C. acnes.

The bacterial species Cutibacterium acnes (C. acnes) was formerly known as Propionibacterium acnes (P. acnes). Based on the results from biochemical and genomic studies, the species was taxonomically reclassified in 2016. C. acnes is a Gram-positive, anaerobic, rod-shaped bacterium which is known to be involved in the development of acne and other pathological conditions. C. acnes strains occur on the skin of most people. C. acnes strains can be pathogenic or non-pathogenic. As used herein, "pathogenic" C. acnes strains are strains that are associated with acne. Assays for the identification and selection of pathogenic and non-pathogenic C. acnes strains are described in WO 2018/073651.

C. acnes has been shown to comprise several distinct, major phylogenetic groups classified as types I, II and III, with the major type I clade being further divided into sub-clades known as types IA, IB and IC (Lomholt and Kilian, 2010). Sub-clade IA has been further subdivided into IA1 and IA2 (McDowell et al., 2012). Preferably, the at least one strain of the species C. acnes is a non-pathogenic strain of C. acnes. A genetic analysis of C. acnes strains revealed that strains which are non-pathogenic and not associated with acne are mainly members of (i) clade I, sub-clade IA2, (ii) clade I, sub-clade IB and (ii) clade II.

Accordingly, in one embodiment of the invention, the at least one strain of the species C. acnes belongs either to one of sub-clades IA2, IB of clade I or to clade II. In one embodiment, the at least one strain of the species C. acnes belongs to sub-clade IA2. In another embodiment, the at least one strain of the species C. acnes belongs to sub-clade IB. In yet another embodiment, the at least one strain of the species C. acnes belongs to clade II. If more than one strain is used in the skin care composition of the present invention, it is preferred that strains from different clades or sub-clades are mixed with each other. For example, in one embodiment, the skin care composition comprises at least one strain from sub-clade IA2 and at least one strain from sub-clade IB. In another embodiment, the skin care composition comprises at least one strain from sub-clade IA2 and at least one strain from clade II. In yet another embodiment, the skin care composition comprises at least one strain from sub-clade IB and at least one strain from clade II.

In other embodiments, the skin care composition of the present invention may comprise a mixture of C. acnes strains that include one or more clade I strains and one or more clade II strains. While clade II strains, as indicated above, may be less pathogenic than clade I strains, these strains can also be slower-growing than clade I strains, and less likely to be able to colonize the skin on their own. Accordingly, it may in some embodiments be advantageous that the skin care composition includes a mixture of strains that include both clade I and clade II strains which allow for comparatively improved colonization of the skin by clade II strains.

Non-limiting examples for non-pathogenic strains of *C. acnes* include, but are not limited to, SLST type strains D1, A5, C1, C3, H1, H2, H3, K1, K2, K4, K6, K8, K9, L1, and F4. It is particularly preferred that the skin care composition of the present invention includes at least one SLST type C3 strain and/or at least one SLST type K8 strain. In one embodiment, the skin care composition of the present invention includes at least one SLST type C3 strain, and more preferably two or more SLST type C3 strains, such as 2, 3, 4, 5, 6, 7, 8, 9 or 10 SLST type C3 strains. In another embodiment, the skin care composition of the present invention includes at least one SLST type K8 strain, and more preferably two or more SLST type K8 strains, such as 2, 3, 4, 5, 6, 7, 8, 9 or 10 SLST type K8 strains. In yet another embodiment, the skin care composition of the present invention includes at least one SLST type C3 strain in combination with at least one SLST type K8 strain. In yet another embodiment, the skin care composition of the present invention includes two or more SLST type C3 strains in combination with at least one SLST type K8 strain. In yet another embodiment, the skin care composition of the present invention includes at least one SLST type C3 strain in combination with two or more SLST type K8 strains. In yet another embodiment, the skin care composition of the present invention includes two or more SLST type C3 strains in combination with two or more SLST type K8 strains. In some embodiments, the one or more SLST type C3 strains and the one or more SLST type K8 strains are at approximately equal concentrations within the composition. In other embodiments, the one or more SLST type C3 strains are at a higher concentration than the one or more SLST type K8 strains within the composition. In other embodiments, the one or more SLST type C3 strains are at a lower concentration than the one or more SLST type K8 strains within the composition.

In a particularly preferred embodiment, the skin care composition of the present invention includes the SLST type C3 strain that was deposited under the Budapest Treaty by S-Biomedic N.V. (Turnhoutsweg 30, 2340 Beerse, Belgium) at the Leibniz Institute DSMZ—German Collection of Microorganisms and Cell Cultures, Inhoffenstr. 7B, D-38124 Braunschweig, Germany on Oct. 19, 2017 under accession number DSM 32667. In another particularly preferred embodiment, the skin care composition of the present invention includes the SLST type K8 strain that was deposited under the Budapest Treaty by S-Biomedic N.V. (Turnhoutsweg 30, 2340 Beerse, Belgium) at the Leibniz Institute DSMZ—German Collection of Microorganisms and Cell Cultures, Inhoffenstr. 7B, D-38124 Braunschweig, Germany on Oct. 19, 2017 under accession number DSM 32668. In yet another preferred embodiment, the skin care composition of the present invention includes both the SLST type C3 strain DSM 32667 and the SLST type K8 strain DSM 32668. In another embodiment, the skin care composition comprising the at least one SLST type C3 strain and the at least one SLST type K8 strain additionally comprises at least one SLST type A5 strain and/or at least one SLST type F4 strain. Accordingly, in one embodiment, the composition comprises at least one SLST type C3 strain, at least one SLST type K8 strain, and at least one SLST type A5 strain. In another embodiment, the composition comprises at least one SLST type C3 strain, at least one SLST type K8 strain, and at least one SLST type F4 strain. In yet another embodiment, the composition comprises at least one SLST type C3 strain, at least one SLST type K8 strain, at least one SLST type A5 strain and at least one SLST type F4 strain.

The strains designation referred to herein is based on the single-locus sequence typing (SLST) scheme described in Scholz et al. 2014 using locus PPA2385 as the SLST target sequence. The sequences of the PPA2385 locus of the different strains identified by Scholz are listed as SEQ ID NO:1-76 herein. Accordingly, a "SLST type C3" strain is a strain that comprises in its genome a sequence of the PPA2385 locus which is 100% identical to the sequence depicted in SEQ ID NO:27. Similarly, a "SLST type K8" strain is a strain that comprises in its genome a sequence of the PPA2385 locus which is 100% identical to the sequence as depicted in SEQ ID NO:64. The SLST scheme is also described in more detail in WO 2018/073651. Sequence identification of the PPA2385 locus can be performed as described in WO 2018/073651 by PCR amplification and DNA sequencing using the nucleotide primer set forth in SEQ ID NO:77-82. Based on the information presented herein and in WO 2018/073651, one of ordinary skill in the art would understand how *C. acnes* strains could be identified and classified.

The composition the present invention may include both pathogenic strains and non-pathogenic strains of *C. acnes*. However, in a preferred embodiment of the invention, the skin care composition comprises exclusively non-pathogenic strains of *C. acnes*. It is particularly preferred that the skin care composition of the invention does not include a ribotype 6 (RT6) strain of *C. acnes*. The ribotype classification system is based on differences in the 16S rDNA sequence between different strains of *C. acnes*. The ribotype system is explained, for example, in Fitz-Gibbon et al. 2013. It is further particularly preferred that the skin care composition of the invention does not include a Phenotype III strain of *C. acnes*.

*C. acnes* strains are normally able to produce the signaling molecule trans-10, cis-12 linoleic acid from its precursor molecule linoleic acid, the latter of which is naturally present in the sebum (Rosson et al., 2004). Trans-10, cis-12 linoleic acid is thought to stimulate sebum production and secretion, which is important for *C. acnes* colonization of the skin. In this way, trans-10, cis-12 linoleic acid promotes the onset of acne (Downing et al., 1986; Letawe et al., 1998). Dependent on the skin of a subject, it may be favorable to either reduce or increase sebum production. For example, it may be useful to reduce sebum production in skin of a subject suffering from acne or oily skin. To the contrary, it may be useful to increase sebum production in skin of a subject suffering from dry skin.

In one embodiment, the one or more *C. acnes* strains to be included into the skin care compositions of the present invention are hence selected based on its ability to produce trans-10, cis-12 linoleic acid. In one preferred embodiment, strains that produce low levels of trans-10, cis-12 linoleic acid are selected for inclusion into the skin care compositions of the invention which are to be used against acne or oily skin. Without wishing to be bound by theory, these strains are thought to reduce sebum production, which is useful for preventing or reducing the symptoms of acne or oily skin. SLST type strains C3, C1, F4, A5, K1, K2, K8 and L1 produce only low amounts of trans-10, cis-12 linoleic acid. In another preferred embodiment, strains that produce high levels of trans-10, cis-12 linoleic acid are selected for inclusion into the skin care compositions of the invention which are to be used against dry skin. Without wishing to be bound by theory, these strains are thought to increase sebum production, which is useful for preventing or reducing the symptoms of dry skin. SLST type strain A1 produces high amounts of trans-10, cis-12 linoleic acid.

In one embodiment, the one or more *C. acnes* strains to be included into the skin care compositions of the present invention have been isolated from the skin microbiome of a donor subject. The subject may not be afflicted with acne or oily skin or may suffer from mild, moderate or severe acne. In another embodiment, the strains that have been isolated from the skin microbiome of a donor subject are non-pathogenic strains.

The skin care composition of the present invention may also comprise one or more genetically modified strains of *C. acnes*. In another embodiment, the skin care composition comprises one or more genetically modified of *C. acnes* in combination with one or more naturally occurring strains of *C. acnes*. The genetically modified strains have preferably been modified to produce lower or higher amounts of trans-10, cis-12 linoleic acid. The production of trans-10, cis-12 linoleic acid can be detected as described in U.S. Pat. No. 6,743,609 or by other commonly known methods, such as FAME (fatty acid methyl esters) or gas chromatography. In certain other embodiments, the skin care composition of the present invention only comprises naturally occurring strains of *C. acnes*, i.e., only comprises strain(s) of *C. acnes* that have not been genetically modified by man.

It is particularly preferred that the at least one *C. acnes* strain is present in the composition in an amount of $1.0 \times 10^4$-$1.0 \times 10^{11}$ colony forming units (CFU) per ml, more preferably $1.0 \times 10^5$-$1.0 \times 10^{10}$ CFU/ml, and even more preferably $1.0 \times 10^7$-$1.0 \times 10^{10}$ CFU/ml, or $1.0 \times 10^8$-$1.0 \times 10^{10}$ CFU/ml. For example, the at least one *C. acnes* strain may be present in an amount of at least $1.0 \times 10^5$ CFU/ml, preferably at least $1.0 \times 10^6$ CFU/ml, more preferably at least $1.0 \times 10^7$ CFU/ml, such as at least $1.0 \times 10^8$ CFU/ml, at least $1.0 \times 10^9$ CFU/ml, or at least $1.0 \times 10^{10}$ CFU/ml of the skin care composition. It is particularly preferred that the at least one *C. acnes* strain is present in an amount of at least $1.0 \times 10^{10}$ CFU/ml, $2.0 \times 10^{10}$ CFU/ml, $3.0 \times 10^{10}$ CFU/ml, $4.0 \times 10^{10}$ CFU/ml, $5.0 \times 10^{10}$ CFU/ml, $6.0 \times 10^{10}$ CFU/ml, $7.0 \times 10^{10}$ CFU/ml, $8.0 \times 10^{10}$ CFU/ml, or $9.0 \times 10^{10}$ CFU/ml of the skin care composition.

In some embodiments, each of the *C. acnes* strains that is present in the composition is present in an amount of $1.0 \times 10^4$-$1.0 \times 10^{11}$ CFU/ml, more preferably $1.0 \times 10^5$-$1.0 \times 10^{10}$ CFU/ml, and even more preferably $1.0 \times 10^7$-$1.0 \times 10^{10}$ CFU/ml, or $1.0 \times 10^8$-$1.0 \times 10^{10}$ CFU/ml. For example, each of the *C. acnes* strains may be present in an amount of at least $1.0 \times 10^5$ CFU/ml, preferably at least $1.0 \times 10^6$ CFU/ml, more preferably at least $1.0 \times 10^7$ CFU/ml, such as at least $1.0 \times 10^8$ CFU/ml, at least $1.0 \times 10^9$ CFU/ml, or at least $1.0 \times 10^{10}$ CFU/ml of the skin care composition. It is particularly preferred that each of the *C. acnes* strains is present in an amount of at least $1.0 \times 10^{10}$ CFU/ml, $2.0 \times 10^{10}$ CFU/ml, $3.0 \times 10^{10}$ CFU/ml, $4.0 \times 10^{10}$ CFU/ml, $5.0 \times 10^{10}$ CFU/ml, $6.0 \times 10^{10}$ CFU/ml, $7.0 \times 10^{10}$ CFU/ml, $8.0 \times 10^{10}$ CFU/ml, or $9.0 \times 10^{10}$ CFU/ml of the skin care composition. For example, if the skin care composition of the present invention comprises one SLST type C3 strain and one SLST type K8 strain, each of these strains may be present in an amount of $1.0 \times 10^4$-$1.0 \times 10^{11}$ CFU/ml, such as $1.0 \times 10^{10}$ CFU/ml, $2.0 \times 10^{10}$ CFU/ml, $3.0 \times 10^{10}$ CFU/ml, $4.0 \times 10^{10}$ CFU/ml, $5.0 \times 10^{10}$ CFU/ml, $6.0 \times 10^{10}$ CFU/ml, $7.0 \times 10^{10}$ CFU/ml, $8.0 \times 10^{10}$ CFU/ml, or $9.0 \times 10^{10}$ CFU/ml.

In some embodiments, the overall amount of lyophilized or spray-dried bacteria in the composition is $1.0 \times 10^4$-$1.0 \times 10^{11}$ CFU/ml, more preferably $1.0 \times 10^5$-$1.0 \times 10^{10}$ CFU/ml, and even more preferably $1.0 \times 10^7$-$1.0 \times 10^{10}$ CFU/ml, or $1.0 \times 10^8$-$1.0 \times 10^{10}$ CFU/ml. For example, the bacteria may be collectively present in the composition in an amount of at least $1.0 \times 10^5$ CFU/ml, preferably at least $1.0 \times 10^6$ CFU/ml, more preferably at least $1.0 \times 10^7$ CFU/ml, such as at least $1.0 \times 10^8$ CFU/ml, at least $1.0 \times 10^9$ CFU/ml, or at least $1.0 \times 10^{10}$ CFU/ml of the skin care composition. It is particularly preferred that the bacteria are collectively present in the composition in an amount of at least $1.0 \times 10^{10}$ CFU/ml, $2.0 \times 10^{10}$ CFU/ml, $3.0 \times 10^{10}$ CFU/ml, $4.0 \times 10^{10}$ CFU/ml, $5.0 \times 10^{10}$ CFU/ml, $6.0 \times 10^{10}$ CFU/ml, $7.0 \times 10^{10}$ CFU/ml, $8.0 \times 10^{10}$ CFU/ml, or $9.0 \times 10^{10}$ CFU/ml of the skin care composition. One of ordinary skill in the art will be readily able to determine the amount of bacteria in a lyophilized or spray-dried composition.

Preferred Compositions

The above components described as being suitable for use in the skin care composition of the present invention can be combined with each other without limitation. Accordingly, skin care compositions of the inventions may comprise, apart from the lyophilized or spray-dried live bacteria of at least one *C. acnes* strain and the thickener, at least one excipient selected from the group consisting of emollients, fillers, antioxidants, preservatives, solubilizers, and pH adjusters, wherein said one or more excipients do not interfere with viability and reactivation of growth of said lyophilized or spray-dried live bacteria. Particularly preferred skin care compositions covered by the instant disclosure are described in the following.

A preferred skincare composition comprises
(a) lyophilized or spray-dried live bacteria of at least one *C. acnes* strain; and
(b) 0.01 to 2.5% (w/w) PEG-40 hydrogenated castor oil, and preferably 0.5 to 1.0% (w/w) PEG-40 hydrogenated castor oil.

Another preferred skincare composition comprises
(a) lyophilized or spray-dried live bacteria of at least one *C. acnes* strain selected from the group consisting of SLST type strains D1, A5, C1, C3, H1, H2, H3, K1, K2, K4, K6, K8, K9, L1, and F4; and
(b) 0.01 to 2.5% (w/w) PEG-40 hydrogenated castor oil, and preferably 0.5 to 1.0% (w/w) PEG-40 hydrogenated castor oil.

Another preferred skincare composition comprises
(a) lyophilized or spray-dried live bacteria of at least one *C. acnes* SLST type C3 strain and at least one *C. acnes* SLST type K8 strain; and
(b) 0.01 to 2.5% (w/w) PEG-40 hydrogenated castor oil, and preferably 0.5 to 1.0% (w/w) PEG-40 hydrogenated castor oil.

Another preferred skincare composition comprises
(a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;
(b) 0.05 to 25.0% (w/w) dicaprylyl carbonate, and preferably 7.5 to 10.0% (w/w) dicaprylyl carbonate; and
(c) 0.01 to 2.5% (w/w) PEG-40 hydrogenated castor oil, and preferably 0.5 to 1.0% (w/w) PEG-40 hydrogenated castor oil.

Another preferred skincare composition comprises
(a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;
(b) 0.05 to 25.0% (w/w) ethylhexyl cocoate, and preferably 7.5 to 10.0% (w/w) ethylhexyl cocoate; and (c) 0.01 to 2.5% (w/w) PEG-40 hydrogenated castor oil, and preferably 0.5 to 1.0% (w/w) PEG-40 hydrogenated castor oil.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.05 to 7.5% (w/w) of a *C. crispus* extract, and preferably 0.2 to 1.5% (w/w) of a *C. crispus* extract; and (c) 0.01 to 2.5% (w/w) PEG-40 hydrogenated castor oil, and preferably 0.5 to 1.0% (w/w) PEG-40 hydrogenated castor oil.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.05 to 10.0% (w/w) hydroxypropyl starch phosphate, and preferably 2.0 to 4.0% (w/w) hydroxypropyl starch phosphate; and (c) 0.01 to 2.5% (w/w) PEG-40 hydrogenated castor oil, and preferably 0.5 to 1.0% (w/w) PEG-40 hydrogenated castor oil.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.01 to 2.5% (w/w) PEG-40 hydrogenated castor oil, and preferably 0.5 to 1.0% (w/w) PEG-40 hydrogenated castor oil; and (c) a citric acid/citrate buffer that provides for a pH of the composition of about 4.0 to about 7.0.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.05 to 5.0% (w/w) distarch phosphate, and preferably 2.0 to 3.0% (w/w) distarch phosphate; and (c) 0.01 to 2.5% (w/w) PEG-40 hydrogenated castor oil, and preferably 0.5 to 1.0% (w/w) PEG-40 hydrogenated castor oil.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.05 to 5.0% (w/w) tapioca starch, and preferably 2.0 to 3.0% (w/w) tapioca starch; and (c) 0.01 to 2.5% (w/w) PEG-40 hydrogenated castor oil, and preferably 0.5 to 1.0% (w/w) PEG-40 hydrogenated castor oil.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.01 to 2.5% (w/w) PEG-40 hydrogenated castor oil, and preferably 0.5 to 1.0% (w/w) PEG-40 hydrogenated castor oil; and (c) 0.01 to 2.0% (w/w) tocopherol, and preferably 0.1 to 1.0% (w/w) tocopherol.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.01 to 2.5% (w/w) PEG-40 hydrogenated castor oil, and preferably 0.5 to 1.0% (w/w) PEG-40 hydrogenated castor oil; and (c) 0.01 to 2.0% (w/w) tocopheryl acetate, and preferably 0.1 to 1.0% (w/w) tocopheryl acetate.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.01 to 2.5% (w/w) PEG-40 hydrogenated castor oil, and preferably 0.5 to 1.0% (w/w) PEG-40 hydrogenated castor oil; and (c) 0.5 to 20.0% (w/w) ethanol, and preferably 8.0 to 15.0% (w/w) ethanol.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.01 to 2.5% (w/w) PEG-40 hydrogenated castor oil, and preferably 0.5 to 1.0% (w/w) PEG-40 hydrogenated castor oil; and (c) 0.05 to 0.5% (w/w) phenoxyethanol, and preferably 0.1 to 0.2% (w/w) phenoxyethanol.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.01 to 2.5% (w/w) PEG-40 hydrogenated castor oil, and preferably 0.5 to 1.0% (w/w) PEG-40 hydrogenated castor oil; and (c) 0.05 to 0.5% (w/w) caprylyl glycol, and preferably 0.1 to 0.2% (w/w) caprylyl glycol.

Another preferred skincare composition comprises (a) lyophilized or spray-dried live bacteria of at least one *C. acnes* strain, preferably lyophilized or spray-dried live bacteria of at least one *C. acnes* SLST type C3 strain and at least one *C. acnes* SLST type K8 strain;

(b) 0.01 to 2.5% (w/w) PEG-40 hydrogenated castor oil, and preferably 0.5 to 1.0% (w/w) PEG-40 hydrogenated castor oil; and (c) 0.05 to 5.0% (w/w) methylpropanediol, and preferably 1.0 to 5.0% (w/w) methylpropanediol.

Cosmetic and Therapeutic Uses

The skin care composition described hereinabove are useful for the modulation of the skin microbiome, and in particular for maintaining healthy skin, such as skin that is free of acne. Compositions comprising at least one live *C. acnes* bacterial strain can help skin to revert microbiome disease states to healthy microbiome states. In one preferred embodiment, the skin care composition is used for preventing the formation of acne or treating acne. In another preferred embodiment, the skin care composition is used for preventing the reoccurrence of acne in a subject who has received a standard acne treatment. It is particularly preferred that the subject is a human.

In one aspect, the invention provides a skin care composition as described hereinabove for use in a method of improving the appearance of the skin of a subject and/or modulating (e.g. increasing or decreasing) the sebum production of skin cells of a subject and/or maintaining healthy skin, such as skin that is free of acne, of a subject. In yet another aspect, the invention relates to the use of a skin care composition as described hereinabove for improving the appearance of the skin of a subject and/or for modulating (e.g. increasing or decreasing) the sebum production of skin cells of a subject and/or for maintaining healthy skin, such as skin that is free of acne, of a subject. In one aspect, the invention provides a skin care composition as described hereinabove for use in a method of treating or preventing a condition selected from the group consisting of acne, oily skin, progressive macular hypomelanosis, dandruff, atopic eczema, atopic dermatitis and rosacea in a subject. It is particularly preferred that the subject is a human.

Methods for treating the skin of a subject by administering a skin care composition as described hereinabove are also provided. These methods may be cosmetic or therapeutic methods. In one aspect a method of improving the appearance of the skin of a subject and/or modulating the sebum production of skin cells of a subject and/or maintaining healthy skin of a subject is provided, said method comprising the topical administration of a skin care composition as described hereinabove. In another aspect, the invention provides a method of treating or preventing a condition selected from the group consisting of acne, oily skin, progressive macular hypomelanosis, dandruff, atopic eczema, atopic dermatitis and rosacea in a subject, said method comprising the topical administration of a skin care composition described hereinabove. It is particularly preferred that the subject is a human.

When the compositions are applied to the skin, it is preferred that the amount of the composition applied to the skin is between 0.5 g and 2.0 g, more preferably between 0.5 g and 1.0 g. Stated differently, the amount of the composition may correspond to at least $1.0 \times 10^5$ CFU, at least $1.0 \times 10^6$ CFU, at least $1.0 \times 10^7$ CFU, at least $1.5 \times 10^7$ CFU, at least $2.0 \times 10^7$ CFU, or at least $2.5 \times 10^7$ CFU.

Ready-to-Use Compositions and Kit-of-Parts

The skin care composition of the present invention may be provided as ready-to-use composition which is suitable for direct topical administration to the skin. Such a composition may be provided in different forms, including, but not limited to, in the form of a gel, cream, lotion, ointment, paste, soft paste, suspension; solution, salve, wax, milk, emulsion, or the like. In such a composition, the lyophilized or spray-dried live bacteria will be present in admixture with other cosmetic or pharmaceutical excipients described elsewhere herein, such as emollients, fillers, and the like. Upon application of these compositions to the skin, the dried bacteria will be re-activated on the skin of the subject to which the product is applied. Growth of the re-activated bacteria from the skin care composition will positively influence the microbial flora on the skin of the subject.

These ready-to-use compositions are preferably stable at room temperature for at least 1 week, at least 2, weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks or more than 30 weeks. Stated differently, such compositions are preferably stable at room temperature for at least 1 month, at least 2 months, at least 3 months, at least 4 months, at least 5 months, at least 6 months or more than 6 months. As used herein, a composition is regarded as being stable if the reduction in the number of colony forming units present in the composition after storage is less than a 3 log reduction, preferably less than a 2 log reduction, and more preferably less than a 1 log reduction. Stated differently, a composition is regarded as being stable if the reduction in the number of colony forming units present in the composition after storage is less than 1000-fold, preferably less than 100-fold, and more preferably less 10-fold relative to the number of colony forming units in the composition before storage.

The skin care compositions of the present invention may alternatively be provided as a kit-of-parts in which the lyophilized or spray-dried bacteria are spatially separated from the other components, e.g. the cosmetic or therapeutic components. For example, the kit-of-parts may be in the form of a packaging with two spatially separated chambers, wherein the first chamber contains the lyophilized or spray-dried bacteria, and the second chamber contains a cosmetic preparation, such as a water-containing cosmetic preparation. Prior to use, the contents of both chambers are mixed with each other, such as for example by a consumer or a patient, to provide a homogeneous skin care composition which is then applied to the skin. A kit-of-part assembly has the advantage that the bacteria can remain in lyophilized or spray-dried form until use which is associated with a particular high storage stability of the composition. In a kit-of-parts assembly, it is advantageous if the weight ratio of the bacteria in the first chamber to the cosmetic preparation, in particular the water-containing cosmetic preparation, in the second chamber is from 1:10 to 1:100, such as 1:10, 1:20, 1:30, 1:40, 1:50, 1:60, 1:70, 1:80, 1:90, or 1:100. After mixing the contents of both chambers, the skin care composition contains preferably 1-10% by weight lyophilized or spray-dried bacteria and 99-90% by weight of the cosmetic preparation, e.g. the water-containing cosmetic preparation. According to the present invention a kit-of-parts can be provided, for example, in a Lyo-Ject® double-chamber syringe, in a V-LK® double-chamber carpuel or in a dual-chamber system as described in WO2018077598 A1. In another preferred embodiment, the lyophilized or spray-dried bacteria in the first chamber may be suspended in a lipid or oil. This will significantly facilitate packaging and filling. In addition, the surrounding lipid or oil will protect the bacteria from premature rehydration. Preferably, the bacteria are suspended in ethylhexyl cocoate or dicaprylyl carbonate. The weight ratio of the bacteria to the oil or lipid preferably is between 1:1 and 1:2.

In one embodiment, the skin care composition of the present invention is an aqueous preparation, such as a gel. Aqueous preparations as intended herein encompass aqueous solutions, as well as aqueous dispersions. In one embodiment, the skin care composition is an oil-in-water emulsion. If the skin care composition contains an oil phase, e.g. when using an oil-in-water emulsion, it is preferred that the oil phase contains triglycerides and/or octyldodecanol. In addition, the oil phase may contain one or more oils selected from the group of lecithin, olive oil, sunflower oil, jojoba oil, soya oil, peanut oil, rapeseed oil, almond oil, palm oil, coconut oil, castor oil, wheat germ oil, grape seed oil, safflower oil, evening primrose oil, macadamia nut oil and the like.

The term "comprising", when used in the context with methods or compositions, means that other method steps or components of the composition can be present in addition to the method steps or components presented. The use of the term "comprising" indicates inclusion rather than limitation.

For example, a composition "comprising" components A+B may also comprise C as a further component. Similarly, a method "comprising" steps (a) and (b) may also comprise (c) as a further method step. In contrast, the term "consisting of", when used in the context with methods or compositions, refers to methods or compositions which are exclusive of any other method steps or components of the composition not recited in the description of the respective composition or method. For example, a composition "consisting of" components A+B is limited to these two components and does not contain any other component apart from A and B. Similarly, a method "consisting of" steps (a) and (b) is a two-step method and does not contain any other method steps apart from (a) and (b). It should be understood, however, that any method or composition described herein as "comprising" certain method steps or components may preferably "consist essentially of" or may more preferably "consist of" the recited method steps or components. Further, unless otherwise required by context, singular terms shall include pluralities and plural terms shall include the singular.

LITERATURE

Bek-Thomsen, M., Lomholt, H. B., and Kilian, M. (2008). Acne is not associated with yet-uncultured bacteria. J. Clin. Microbiol. 46, 3355-3360.

Belkaid, Y., and Segre, J. A. (2014). Dialogue between skin microbiota and immunity. Science 346, 954-959.

Downing, D. T., Stewart, M. E., Wertz, P. W., and Strauss, J. S. (1986). Essential fatty acids and acne. J. Am. Acad. Dermatol. 14, 221-225.

Fitz-Gibbon, S., Tomida, S., Chiu, B.-H., Nguyen, L., Du, C., Liu, M., Elashoff, D., Erfe, M. C., Loncaric, A., Kim, J., et al. (2013). Propionibacterium acnes strain populations in the human skin microbiome associated with acne. J. Invest. Dermatol. 133, 2152-2160.

Grice, E. A., and Segre, J. A. (2011). The skin microbiome. Nat. Rev. Microbiol. 9, 244-253.

Holmes, A D. (2013). Potential role of microorganisms in the pathogenesis of rosacea. J. Am. Acad. Dermatol. 69, 1025-1032.

Kong, H. H., Oh, J., Deming, C., Conlan, S., Grice, E. A., Beatson, M. A., Nomicos, E., Polley, E. C., Komarow, H. D., Murray, P. R., et al. (2012). Temporal shifts in the skin microbiome associated with disease flares and treatment in children with atopic dermatitis. Genome Res. 22, 850-859.

Letawe, C., Boone, M., and Piérard, G. E. (1998). Digital image analysis of the effect of topically applied linoleic acid on acne microcomedones. Clin. Exp. Dermatol. 23, 56-58.

Lomholt, H. B., and Kilian, M. (2010). Population Genetic Analysis of Propionibacterium acnes Identifies a Sub-population and Epidemic Clones Associated with Acne. PLoS ONE 5.

McDowell, A., Barnard, E., Nagy, I., Gao, A., Tomida, S., Li, H., Eady, A., Cove, J., Nord, C. E., and Patrick, S. (2012). An Expanded Multilocus Sequence Typing Scheme for Propionibacterium acnes: Investigation of "Pathogenic", "Commensal" and Antibiotic Resistant Strains. PLoS ONE 7, e41480.

Oh, J., Byrd, A. L., Deming, C., Conlan, S., NISC Comparative Sequencing Program, Kong, H. H., and Segre, J. A. (2014). Biogeography and individuality shape function in the human skin metagenome. Nature 514, 59-64.

Rosson, R. A., Grund, A. D., Deng, M.-D., and Sanchez-Riera, F. (2004). Linoleate isomerase.

Scholz, C. F. P., Jensen, A., Lomholt, H. B., Brüggemann, H., and Kilian, M. (2014). A Novel High-Resolution Single Locus Sequence Typing Scheme for Mixed Populations of Propionibacterium acnes In Vivo. PLoS ONE 9, e104199.

DETAILED DESCRIPTION OF EXEMPLARY EMBODIMENTS OF THE INVENTION

Examples

The present invention is further illustrated by the following examples, which in no way should be construed as further limiting. The entire contents of all of the references (including literature references, issued patents, published patent applications, and co pending patent applications) cited throughout this application are hereby expressly incorporated by reference.

Example 1: Evaluation of the Minimum Inhibitory Concentration (MIC)

In microbiology, the MIC is the lowest concentration of a chemical which prevents visible growth of bacterium. The resulted MIC value depends both on the microorganism and the test compound. The MIC is determined by preparing concentrations series of the test compound in vitro, incubating the solutions with the separate batches of cultured bacteria, and measuring the results using agar dilution or broth microdilution. For the experiments with C. acnes strains C3 and K8, media comprising yeast extract soy peptone and dextrose were used. The MIC is determined by turbidity.

A total of 125 cosmetic excipients were tested for their compatibility with C. acnes strains C3 and K8. Hydrophilic compounds were tested in a 96-well plate liquid broth format, poorly soluble compounds were pre-dissolved in DMSO before dilution in liquid broth and hydrophobic or solid compounds were tested in an agar well diffusion test assay. The different dilutions of the test excipients in media were prepared in Falcon tubes and then distributed in a deep well plate using a multistepper. Each well received 1.2 ml and was subsequently inoculated with 120 µl of C. acnes bacteria suspension (strain C3 and K8). From the deep well plate 200 µl were transferred in each well of a clear 96 well replicate plate. The leftover was discarded. The plates were then incubated anaerobically for 3 days at 37° C. Following incubation, the test plates were visually examined and wells were scored for growth or complete growth inhibition to define the minimum inhibitory concentration.

Results:

It was found that the compatibility of standard excipients for the bacterial strains widely varied. Only few excipients did not lead to inhibition or significant inhibition. These excipients are listed in the below table with their compatibility values for C. acnes strains C3 and K8. The compatibility values represent the MIC value of the listed ingredients with the tested C. acnes strains. At this concentration [% w/vol] the tested compound starts interfering with the growth of the tested strains. The compounds can be used in formulations at concentrations below this concentration.

The results obtained from MIC testing are depicted in the below Table 1.

| INCI | FUNCTION | COMPATABILITY VALUE C3 [%] | COMPATABILITY VALUE K8 [%] |
|---|---|---|---|
| dicaprylyl carbonate + tocopherol | emollient | 10.00 | 10.00 |
| ethylhexyl cocoate | emollient | 10.00 | 10.00 |
| Chondrus crispus extract | thickener | 5.00 | 5.00 |
| hydroxypropyl starch phosphate + aqua | thickener | 1.00 | 1.00 |
| distarch phosphate | filler | 5.00 | 5.00 |
| tapioca starch + aqua | filler | 5.00 | 5.00 |
| tocopherol | antioxidant | 1.50 | 1.50 |
| tocopheryl acetate | antioxidant | 1.00 | 1.00 |
| ethanol | preservative | 3.75 | 3.75 |
| phenoxyethanol | preservative | 0.45 | 0.23 |
| caprylyl glycol | preservative | 0.18 | 0.18 |
| methylpropanediol | preservative | 4.00 | 4.00 |
| peg-40 hydrogenated castor oil | solubilizer | 1.00 | 1.00 |
| citric acid | buffering | 0.33 | 0.08 |
| Citric acid/citrate | buffering | 1.30 | 1.30 |

Example 2: Reactivation Assay of Freeze Dried Bacteria in Prototype Formulations Based on the results from the MIC testing, a set of 15 prototype formulations were designed to test for efficient reactivation of freeze-dried *C. acnes* bacteria. For this purpose, a freeze-dried powder of *C. acnes* strains K8 and C3 was produced and mixed with other ingredients as indicated below. Ingredients are listed in % (w/w). The formulations were provided in two pre-mixed compositions A and B that were finally mixed with each other. The following formulations were made:

| Formulation 1 | | |
|---|---|---|
| A | Isopropyl Palmitate | 20.000 |
| | Carrageenan | 1.000 |
| | Sodium chloride | 0.900 |
| | Sodium citrate | 0.174 |
| | Citric acid | 0.015 |
| | Distarch phosphate | 2.000 |
| | *C. acnes* lyophilisate | 2.800 |
| B | Water | ad 100 |

| Formulation 2 | | |
|---|---|---|
| A | Isopropyl Palmitate | 20.000 |
| | Carrageenan | 1.000 |
| | Distarch phosphate | 2.000 |
| | *C. acnes* lyophilisate | 2.800 |
| B | Sodium chloride | 0.668 |
| | Sodium citrate | 0.129 |
| | Citric acid | 0.064 |
| | Glycerin | 5.565 |
| | Water | ad 100 |

| Formulation 3 | | |
|---|---|---|
| A | Isopropyl Palmitate | 20.000 |
| | Carrageenan | 1.000 |
| | Distarch phosphate | 2.000 |
| | *C. acnes* lyophilisate | 2.800 |
| B | Sodium chloride | 0.668 |
| | Sodium citrate | 0.129 |
| | Citric acid | 0.015 |
| | Glycerin | 5.565 |
| | Ethanol | 8.040 |
| | Water | ad 100 |

| Formulation 4 | | |
|---|---|---|
| A | Isopropyl Palmitate | 20.000 |
| | Distarch phosphate | 2.000 |
| | *C. acnes* lyophilisate | 2.800 |
| B | Carrageenan | 0.075 |
| | Sodium chloride | 0.677 |
| | Sodium citrate | 0.131 |
| | Citric acid | 0.015 |
| | Glycerin | 5.640 |
| | Water | ad 100 |

| Formulation 5 | | |
|---|---|---|
| A | Isopropyl Palmitate | 20.000 |
| | Distarch phosphate | 2.000 |
| | *C. acnes* lyophilisate | 2.800 |
| B | Hydroxyethyl cellulose | 0.451 |
| | Sodium chloride | 0.677 |
| | Sodium citrate | 0.131 |
| | Citric acid | 0.015 |
| | Glycerin | 5.640 |
| | Ethanol | 8.152 |
| | Water | ad 100 |

| Formulation 6 | | |
|---|---|---|
| A | Isopropyl Palmitate | 20.000 |
| | Distarch phosphate | 2.000 |
| | *C. acnes* lyophilisate | 2.800 |
| B | Hydroxypropyl starch phosphate | 3.384 |
| | Sodium chloride | 0.677 |
| | Sodium citrate | 0.131 |
| | Citric acid | 0.008 |
| | Glycerin | 5.640 |
| | Ethanol | 8.152 |
| | Water | ad 100 |

| Formulation 7 | | |
|---|---|---|
| A | Isopropyl Palmitate | 20.000 |
| | Distarch phosphate | 2.000 |
| | *C. acnes* lyophilisate | 2.800 |
| B | Sodium hyaluronate | 0.376 |
| | Carbomer | 0.564 |
| | Sodium chloride | 0.677 |
| | Sodium citrate | 0.131 |
| | Citric acid | 0.008 |
| | Glycerin | 3.760 |

25

-continued

Formulation 7

| | | |
|---|---|---|
| | Ethanol | 8.152 |
| | Caprylyl Glycol | 0.075 |
| | Water | ad 100 |

Formulation 8

| | | |
|---|---|---|
| A | Isopropyl Palmitate | 20.000 |
| | Distarch phosphate | 2.000 |
| | C. acnes lyophilisate | 2.800 |
| B | Sodium hyaluronate | 0.978 |
| | Sodium chloride | 0.677 |
| | Sodium citrate | 0.131 |
| | Citric acid | 0.008 |
| | Glycerin | 3.760 |
| | Ethanol | 8.152 |
| | Caprylyl Glycol | 0.075 |
| | Butylene glycol | 3.760 |
| | Water | ad 100 |

Formulation 9

| | | |
|---|---|---|
| A | Carrageenan | 1.000 |
| | Distarch phosphate | 2.000 |
| | C. acnes lyophilisate | 2.800 |
| B | Sodium chloride | 0.848 |
| | Sodium citrate | 0.164 |
| | Citric acid | 0.019 |
| | Glycerin | 7.065 |
| | Ethanol | 10.211 |
| | Water | ad 100 |

Formulation 10

| | | |
|---|---|---|
| A | Carrageenan | 1.000 |
| | Distarch phosphate | 2.000 |
| | C. acnes lyophilisate | 2.800 |
| B | Sodium chloride | 0.848 |
| | Sodium citrate | 0.164 |
| | Citric acid | 0.019 |
| | Glycerin | 7.065 |
| | Phenoxyethanol | 0.188 |
| | Methylpropanediol | 3.768 |
| | Caprylyl Glycol | 0.094 |
| | Water | ad 100 |

Formulation 11

| | | |
|---|---|---|
| A | C. acnes lyophilisate | 2.800 |
| B | Hydroxyethyl cellulose | 0.583 |
| | Sodium chloride | 0.875 |
| | Sodium citrate | 0.169 |
| | Citric acid | 0.019 |
| | Glycerin | 7.290 |
| | Ethanol | 10.536 |
| | Water | ad 100 |

Formulation 12

| | | |
|---|---|---|
| A | Isopropyl Palmitate | 5.000 |
| | Ethylhexyl cocoate | 10.000 |

26

-continued

Formulation 12

| | | |
|---|---|---|
| | Distarch phosphate | 2.000 |
| | C. acnes lyophilisate | 0.940 |
| B | Hydroxyethyl cellulose | 0.498 |
| | Sodium chloride | 0.747 |
| | Sodium citrate | 0.144 |
| | Citric acid | 0.017 |
| | Glycerin | 6.225 |
| | Ethanol | 9.740 |
| | Water | ad 100 |

Formulation 13

| | | |
|---|---|---|
| A | Dicaprylyl Carbonate | 7.500 |
| | Ethylhexyl cocoate | 7.500 |
| | Distarch phosphate | 2.000 |
| | C. acnes lyophilisate | 0.940 |
| B | Hydroxyethyl cellulose | 0.498 |
| | Sodium chloride | 0.747 |
| | Sodium citrate | 0.144 |
| | Citric acid | 0.017 |
| | Glycerin | 6.225 |
| | Ethanol | 9.740 |
| | Water | ad 100 |

Formulation 14

| | | |
|---|---|---|
| A | Isodecyl neopentanoate | 10.000 |
| | Isopropyl palmitate | 5.000 |
| | Distarch phosphate | 2.000 |
| | C. acnes lyophilisate | 0.940 |
| B | Hydroxyethyl cellulose | 0.498 |
| | Sodium chloride | 0.747 |
| | Sodium citrate | 0.144 |
| | Citric acid | 0.017 |
| | Glycerin | 6.225 |
| | Ethanol | 9.740 |
| | Water | ad 100 |

Formulation 15

| | | |
|---|---|---|
| A | Dicaprylyl ether | 7.500 |
| | Isopropyl palmitate | 7.500 |
| | Distarch phosphate | 2.000 |
| | C. acnes lyophilisate | 0.940 |
| B | Hydroxyethyl cellulose | 0.498 |
| | Sodium chloride | 0.747 |
| | Sodium citrate | 0.144 |
| | Citric acid | 0.017 |
| | Glycerin | 6.225 |
| | Ethanol | 9.740 |
| | Water | ad 100 |

The formulations are depicted in the form of a table in FIG. 1. For formulations 1-11, the CFU target value was $1\times10^7$. For formulations 12-15, the CFU target value was $1\times10^6$. A CFU count was performed directly after mixing the formulation to assess the effect of the prototype formulation on the revival and subsequent stability rate of the bacteria. Briefly, the formula component A (lyophilisate/oil suspension) and the formula component B (hydrogel/aqueous solution) are mixed together and well vortexed. Directly after mixing an aliquot is removed and transferred to 0.9% NaCl. Further dilutions are plated on COST agar plates and incubated anaerobically at 37° C. for 5 days.

Figure 3:
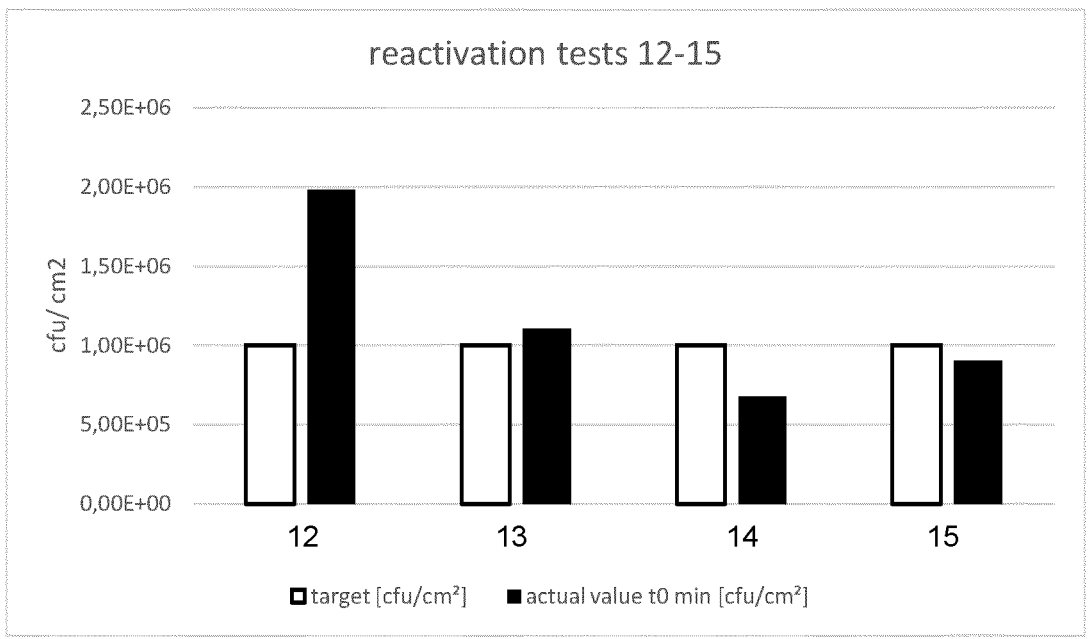
FIG. 3 shows the results from experiments analyzing the reactivation of freeze-dried bacteria from prototype formulations 12-15.

Results:

The results are depicted in FIGS. 2 and 3. It can be seen that all formulations 1-15 showed an acceptable reactivation of the freeze-dried bacteria. There was no negative influence of the ingredients on bacteria reactivation.

Example 3: Reactivation Assay of Freeze Dried Bacteria in Prototype Formulations Similar to the formulations tested in Example 2, another set of 11 prototype formulations was prepared with higher concentrations of the excipients of the invention. The formulations were tested as described in Example 2 for their impact on reactivation of freeze-dried *C. acnes* bacteria. As a control, a formulation containing the lyophilisate and low amounts of the excipients was prepared. The following formulations were made:

| Control | | |
|---|---|---|
| A | Isopropyl Palmitate | 0.050 |
| | Ethylhexyl Cocoate | 0.050 |
| | Distarch phosphate | 0.050 |
| | *C. acnes* lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Ethanol | 0.500 |
| | Water | ad 100 |

| Formulation 1 | | |
|---|---|---|
| A | Isopropyl Palmitate | 0.050 |
| | Ethylhexyl Cocoate | 25.000 |
| | Distarch phosphate | 0.050 |
| | *C. acnes* lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Ethanol | 0.500 |
| | Water | ad 100 |

| Formulation 2 | | |
|---|---|---|
| A | Isopropyl Palmitate | 0.050 |
| | Ethylhexyl Cocoate | 0.050 |
| | Distarch phosphate | 5.000 |
| | *C. acnes* lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Ethanol | 0.500 |
| | Water | ad 100 |

| Formulation 3 | | |
|---|---|---|
| A | Isopropyl Palmitate | 0.050 |
| | Ethylhexyl Cocoate | 0.050 |
| | Distarch phosphate | 0.050 |
| | *C. acnes* lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Ethanol | 20.000 |
| | Water | ad 100 |

| Formulation 4 | | |
|---|---|---|
| A | Isopropyl Palmitate | 0.050 |
| | Ethylhexyl Cocoate | 0.050 |
| | Distarch phosphate | 0.050 |
| | *C. acnes* lyophilisate | 4.710 |
| B | PEG-40 Hydrogenated Castor Oil | 2.500 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Ethanol | 0.500 |
| | Water | ad 100 |

| Formulation 5 | | |
|---|---|---|
| A | Isopropyl Palmitate | 0.050 |
| | Ethylhexyl Cocoate | 0.050 |
| | Dicaprylyl Carbonate | 25.000 |
| | Distarch phosphate | 0.050 |
| | *C. acnes* lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Ethanol | 0.500 |
| | Water | ad 100 |

| Formulation 6 | | |
|---|---|---|
| A | Isopropyl Palmitate | 0.050 |
| | Ethylhexyl Cocoate | 0.050 |
| | Distarch phosphate | 0.050 |
| | *C. acnes* lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Chondrus Crispus Extract | 7.500 |
| | Ethanol | 0.500 |
| | Water | ad 100 |

Formulation 7

| | | |
|---|---|---|
| A | Isopropyl Palmitate | 0.050 |
| | Ethylhexyl Cocoate | 0.050 |
| | Distarch phosphate | 0.050 |
| | C. acnes lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Hydroxypropylstarch Phosphate | 10.000 |
| | Ethanol | 0.500 |
| | Water | ad 100 |

Formulation 8

| | | |
|---|---|---|
| A | Isopropyl Palmitate | 0.050 |
| | Ethylhexyl Cocoate | 0.050 |
| | Distarch phosphate | 0.050 |
| | C. acnes lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Tocopherol | 2.000 |
| | Ethanol | 0.500 |
| | Water | ad 100 |

Formulation 9

| | | |
|---|---|---|
| A | Isopropyl Palmitate | 0.050 |
| | Ethylhexyl Cocoate | 0.050 |
| | Distarch phosphate | 0.050 |
| | C. acnes lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Tocopheryl Acetate | 2.000 |
| | Ethanol | 0.500 |
| | Water | ad 100 |

Formulation 10

| | | |
|---|---|---|
| A | Isopropyl Palmitate | 0.050 |
| | Ethylhexyl Cocoate | 0.050 |
| | Distarch phosphate | 0.050 |
| | Tapioca Starch | 5.000 |
| | C. acnes lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Glycerin | 0.050 |
| | Ethanol | 0.500 |
| | Water | ad 100 |

Formulation 11

| | | |
|---|---|---|
| A | Isopropyl Palmitate | 0.050 |
| | Ethylhexyl Cocoate | 0.050 |
| | Distarch phosphate | 0.050 |
| | C. acnes lyophilisate | 4.710 |
| B | PEG-40 Hydrogenated Castor Oil | 0.010 |
| | Sodium Chloride | 0.050 |
| | Sodium Citrate | 0.010 |
| | Citric Acid | 0.010 |
| | Sodium Hydroxide | 0.001 |
| | Hydroxyethylcellulose | 0.050 |
| | Phenoxyethanol | 0.230 |
| | Caprylyl Glycol | 0.180 |
| | Methylpropanediol | 4.000 |
| | Glycerin | 0.050 |
| | Water | ad 100 |

The formulations are depicted in the form of a table in FIG. 4. For all formulations, the CFU target value was $1 \times 10^9$. A CFU count was performed directly after mixing the formulation, as described above in Example 2, and after 1 hour.

Results:

The results are depicted in FIG. 5. It can be seen that all formulations 1-11 showed an acceptable reactivation of the freeze-dried bacteria. There was no negative influence of the ingredients on bacteria reactivation even at the high concentrations that were used in this experiment.

Example 4: Comparative Reactivation Assays

To compare the excipients identified herein as particularly useful for compositions containing lyophilized or spray-dried live bacteria with other excipients having the same or similar function, comparative formulations V-1 to V-10 were prepared and tested for their influence on bacteria reactivation as described in Example 2. As a positive control, a lyophilisate-containing formulation was used which had been found not to influence bacteria reactivation negatively. The following formulations were made for comparison:

Control

| | | |
|---|---|---|
| A | Isopropyl Palmitate | 6.250 |
| | Ethylhexyl Cocoate | 12.500 |
| | Distarch phosphate | 2.500 |
| | C. acnes lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Hydroxyethylcellulose | 0.444 |
| | Glycerin | 5.553 |
| | Ethanol | 9.625 |
| | Water | ad 100 |

Formulation V-1

| | | |
|---|---|---|
| A | Paraffinum Liquidum | 18.750 |
| | Distarch phosphate | 2.500 |
| | C. acnes lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Hydroxyethylcellulose | 0.444 |
| | Glycerin | 5.553 |

-continued

Formulation V-1

| | | |
|---|---|---|
| Ethanol | 9.625 | |
| Water | ad 100 | |

Formulation V-2

| | | |
|---|---|---|
| A | Octyldodecanol | 18.750 |
| | Distarch phosphate | 2.500 |
| | *C. acnes* lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Hydroxyethylcellulose | 0.444 |
| | Glycerin | 5.553 |
| | Ethanol | 9.625 |
| | Water | ad 100 |

Formulation V-3

| | | |
|---|---|---|
| A | Isopropyl Palmitate | 6.250 |
| | Ethylhexyl Cocoate | 12.500 |
| | Talc | 2.500 |
| | *C. acnes* lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Hydroxyethylcellulose | 0.444 |
| | Glycerin | 5.553 |
| | Ethanol | 9.625 |
| | Water | ad 100 |

Formulation V-4

| | | |
|---|---|---|
| A | Isopropyl Palmitate | 6.250 |
| | Ethylhexyl Cocoate | 12.500 |
| | Polymethylsilsesquioxane | 2.500 |
| | *C. acnes* lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Hydroxyethylcellulose | 0.444 |
| | Glycerin | 5.553 |
| | Ethanol | 9.625 |
| | Water | ad 100 |

Formulation V-5

| | | |
|---|---|---|
| A | Isopropyl Palmitate | 6.250 |
| | Ethylhexyl Cocoate | 12.500 |
| | Distarch Phosphate | 2.500 |
| | *C. acnes* lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Carbomer | 0.444 |

-continued

Formulation V-5

| | | |
|---|---|---|
| Glycerin | 5.553 | |
| Ethanol | 9.625 | |
| Water | ad 100 | |

Formulation V-6

| | | |
|---|---|---|
| A | Isopropyl Palmitate | 6.250 |
| | Ethylhexyl Cocoate | 12.500 |
| | Distarch Phosphate | 2.500 |
| | *C. acnes* lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Alkyl/Acrylate Crosspolymer | 0.444 |
| | Glycerin | 5.553 |
| | Ethanol | 9.625 |
| | Water | ad 100 |

Formulation V-7

| | | |
|---|---|---|
| A | Isopropyl Palmitate | 6.250 |
| | Ethylhexyl Cocoate | 12.500 |
| | Distarch Phosphate | 2.500 |
| | *C. acnes* lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Hydroxyethylcellulose | 0.444 |
| | Glycerin | 5.553 |
| | Ascorbic Acid | 3.000 |
| | Ethanol | 9.625 |
| | Water | ad 100 |

Formulation V-8

| | | |
|---|---|---|
| A | Isopropyl Palmitate | 6.250 |
| | Ethylhexyl Cocoate | 12.500 |
| | Distarch Phosphate | 2.500 |
| | *C. acnes* lyophilisate | 4.710 |
| B | PEG-40 Hydrogenated Castor Oil | 0.370 |
| | Sodium Chloride | 0.677 |
| | Sodium Citrate | 0.129 |
| | Citric Acid | 0.015 |
| | Sodium Hydroxide | 0.013 |
| | Hydroxyethylcellulose | 0.444 |
| | Glycerin | 5.553 |
| | Benzethonium Choride | 0.090 |
| | Water | ad 100 |

Formulation V-9

| | | |
|---|---|---|
| A | Isopropyl Palmitate | 6.250 |
| | Ethylhexyl Cocoate | 12.500 |
| | Distarch Phosphate | 2.500 |
| | *C. acnes* lyophilisate | 4.710 |
| B | Caprylyl/Capryl Glucoside | 1.000 |
| | Sodium Chloride | 0.677 |
| | Sodium Citrate | 0.129 |
| | Citric Acid | 0.015 |
| | Sodium Hydroxide | 0.013 |

-continued

| Formulation V-9 | | |
|---|---|---|
| Hydroxyethylcellulose | 0.444 | |
| Glycerin | 5.553 | |
| Water | ad 100 | |

| Formulation V-10 | | |
|---|---|---|
| A | Isopropyl Palmitate | 6.250 |
| | Ethylhexyl Cocoate | 12.500 |
| | Distarch Phosphate | 2.500 |
| | C. acnes lyophilisate | 4.710 |
| B | Glyceryl Caprylate | 0.300 |
| | Sodium Chloride | 0.677 |
| | Sodium Citrate | 0.129 |
| | Citric Acid | 0.015 |
| | Sodium Hydroxide | 0.013 |

-continued

| Formulation V-10 | | |
|---|---|---|
| Hydroxyethylcellulose | 0.444 | |
| Glycerin | 5.553 | |
| Water | ad 100 | |

The formulations are depicted in the form of a table in FIG. 7. For all formulations, the CFU target value was $1 \times 10^9$. A CFU count was performed directly after mixing the formulation, as described above in Example 2, and also after 1 hour or 6 hours, respectively.

Results:

The results are depicted in FIG. 6. It can be seen that formulations V-1 to V-10 have a clear negative impact on the reactivation of the bacteria. This demonstrates that numerous excipients commonly used in cosmetic preparations negatively interfere with the viability or reactivation of the freeze-dried bacteria used in the present studies.

What is claimed is:

1. A skin care composition, wherein the composition is suitable for topical application to skin and comprises:
   (a) lyophilized and/or spray dried live bacteria of at least one strain of Cutibacterium acnes (C. acnes); and
   (b) PEG-40 hydrogenated castor oil as solubilizer.

2. The skin care composition of claim 1, wherein the composition comprises from 0.01% to 2.5% (w/w) of PEG-40 hydrogenated castor oil.

3. The skin care composition of claim 2, wherein the composition comprises from 0.05% to 1.5% (w/w) of PEG-40 hydrogenated castor oil.

4. The skin care composition of claim 2, wherein the composition comprises from 0.5% to 1.0% (w/w) of PEG-40 hydrogenated castor oil.

5. The skin care composition of claim 1, wherein the composition does not comprise any solubilizer which is different from PEG-40 hydrogenated castor oil.

6. The skin care composition of claim 1, wherein the composition further comprises dicaprylyl carbonate and/or ethylhexyl cocoate as emollient.

7. The skin care composition of claim 1, wherein the composition further comprises Chondrus crispus extract and/or hydroxypropyl starch phosphate as thickener.

8. The skin care composition of claim 1, wherein the composition further comprises distarch phosphate and/or tapioca starch as filler.

9. The skin care composition of claim 1, wherein the composition further comprises one or more of ethanol, phenoxyethanol, caprylyl glycol, methylpropanediol as preservative.

10. The skin care composition of claim 1, wherein the composition further comprises tocopherol and/or tocopheryl acetate as antioxidant.

11. The skin care composition of claim 1, wherein the composition further comprises citric acid/citrate buffer as pH adjuster.

12. The skin care composition of claim 1, wherein the at least one strain of C. acnes comprises at least one of single-locus sequence typing (SLST) type strains D1, A5, C1, C3, H1, H2, H3, K1, K2, K4, K6, K8, K9, L1, F4.

13. The skin care composition of claim 12, wherein the at least one strain of C. acnes comprises at least one SLST type strain C3 and/or at least one SLST type strain K8.

14. The skin care composition of claim 13, wherein the at least one strain of C. acnes further comprises at least one SLST type strain A5.

15. The skin care composition of claim 13, wherein the at least one strain of C. acnes further comprises at least one SLST type strain F4.

16. The skin care composition of claim 1, wherein a concentration of each type of C. acnes strain present in the composition is at least 0.5% (w/v) of the skin care composition.

17. The skin care composition of claim 1, wherein each type of the C. acnes strain in the composition is present in an amount of from $10^4$ to $10^{11}$ CFU/ml.

18. The skin care composition of claim 1, wherein the composition is present in the form of at least one of a gel, a cream, an ointment or a lotion.

19. The skin care composition of claim 1, wherein the composition is capable of treating or preventing one or more of acne, oily skin, progressive macular hypomelanosis, dandruff, atopic eczema, atopic dermatitis, rosacea in a subject.

20. The skin care composition of claim 1, wherein the composition is capable of improving an appearance of skin of a subject and/or of modulating a sebum production of skin cells of a subject and/or of maintaining healthy skin of a subject.

* * * * *